(12) United States Patent
Dickie et al.

(10) Patent No.: US 12,364,460 B2
(45) Date of Patent: Jul. 22, 2025

(54) SYSTEMS AND METHODS FOR PLACING A GATE AND/OR A COLOR BOX DURING ULTRASOUND IMAGING

(71) Applicant: Clarius Mobile Health Corp., Vancouver (CA)

(72) Inventors: Kris Dickie, Vancouver (CA); Laurent Pelissier, North Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 0 days.

(21) Appl. No.: 17/411,746

(22) Filed: Aug. 25, 2021

(65) Prior Publication Data

US 2022/0061810 A1 Mar. 3, 2022

Related U.S. Application Data

(60) Provisional application No. 63/070,108, filed on Aug. 25, 2020.

(51) Int. Cl.
*A61B 8/00* (2006.01)
*G01S 15/89* (2006.01)
*A61B 8/06* (2006.01)

(52) U.S. Cl.
CPC .............. *A61B 8/463* (2013.01); *A61B 8/488* (2013.01); *A61B 8/5223* (2013.01); *G01S 15/8979* (2013.01); *A61B 8/06* (2013.01); *A61B 8/5207* (2013.01)

(58) Field of Classification Search
CPC ....... A61B 8/463; A61B 8/488; A61B 8/5223; A61B 8/06; A61B 8/5207; G01S 15/8979
See application file for complete search history.

(56) References Cited

U.S. PATENT DOCUMENTS

| | | | |
|---|---|---|---|
| 8,092,388 B2 | 1/2012 | Park et al. | |
| 2007/0055153 A1* | 3/2007 | Simopoulos | G16H 30/40 600/437 |
| 2009/0088640 A1* | 4/2009 | Park | G06F 18/2148 707/E17.046 |

(Continued)

OTHER PUBLICATIONS

Master's of Data science, "Decision Tree", 2022, https://www.mastersindatascience.org/learning/machine-learning-algorithms/decision-tree/ (Year: 2023).*

(Continued)

*Primary Examiner* — Joel Lamprecht
*Assistant Examiner* — Brooke Lyn Klein
(74) *Attorney, Agent, or Firm* — Julian Ho; Susan Ben-Oliel

(57) ABSTRACT

A method for positioning one or both of a gate and a color box on an ultrasound image generated during scanning of an anatomical feature using an ultrasound scanner comprises deploying an artificial intelligence (AI) model to execute on a computing device communicably connected to the ultrasound scanner, wherein the AI model is trained so that when the AI model is deployed, the computing device generates a prediction of at least one of an optimal position, size, or angle for the gate and/or an optimal location/size of the color box on the ultrasound image generated during ultrasound scanning of the anatomical feature, thereafter enabling the acquisition of corresponding Doppler mode signals.

13 Claims, 12 Drawing Sheets

(56) References Cited

U.S. PATENT DOCUMENTS

| | | | |
|---|---|---|---|
| 2010/0280383 A1* | 11/2010 | Kim | G06T 7/136 600/453 |
| 2012/0053461 A1* | 3/2012 | Li | G01S 7/52033 600/441 |
| 2012/0303386 A1 | 11/2012 | Zavaleta et al. | |
| 2014/0278548 A1 | 9/2014 | Munro et al. | |
| 2015/0222838 A1* | 8/2015 | Kawabata | G01S 15/8979 348/77 |
| 2018/0256132 A1* | 9/2018 | Halmann | A61B 8/488 |
| 2019/0148011 A1* | 5/2019 | Rao | A61B 8/54 600/437 |
| 2020/0229795 A1 | 7/2020 | Tadross et al. | |
| 2020/0352548 A1 | 11/2020 | Specht et al. | |
| 2020/0383662 A1* | 12/2020 | Urabe | A61B 8/14 |
| 2021/0035296 A1* | 2/2021 | Mahrooghy | G06V 10/26 |
| 2021/0088639 A1 | 3/2021 | Yang | |
| 2021/0401405 A1* | 12/2021 | Guracar | G06F 18/24 |
| 2022/0031288 A1* | 2/2022 | Yamamoto | A61B 8/488 |

OTHER PUBLICATIONS

JinHyeong Park, "AutoGate: Fast and Automatic Doppler Gate Localization in B-mode Echocardiogram", 2008 (Year: 2008).*

Renal Fellow Network, "Basics of Doppler Ultrasound for the Nephologist", 2020 (Year: 2020).*

Scikit, "1.10 Decision trees", 2025 (Year: 2025).*

Aitude, "Decision Tree vs. Random Forest in Machine Learning", Feb. 8, 2020 (Year: 2020).*

Williams, "to Tree or not to Tree? that is the decision", Mar. 6, 2020 (Year: 2020).*

Nilesh Patil, "Automated Ultrasound Doppler Angle Estimation Using Deep Learning", IEEE, 2019 (Year: 2019).*

* cited by examiner

SYSTEMS AND METHODS FOR PLACING A GATE AND/OR A COLOR BOX DURING ULTRASOUND IMAGING

FIELD

The present disclosure relates generally to ultrasound imaging, and in particular, systems and methods for placing a gate or a color box during ultrasound imaging.

BACKGROUND

Ultrasound is a useful, non-invasive imaging technique capable of producing real time images. Ultrasound imaging has an advantage over X-ray imaging in that ultrasound imaging does not involve ionizing radiation.

Ultrasound imaging systems may generally be operated in various Doppler modes that take advantage of the fact that reflected echoes undergo a change in frequency when reflected by moving objects in tissue (e.g., blood in vascular tissue). Some Doppler modes include: spectral Doppler, pulsed wave (PW) Doppler, continuous wave (CW) Doppler, color Doppler, and Power Doppler. Tissue Doppler Imaging (TDI) is also a particular way of using spectral or Color Doppler for visualizing tissue wall motion using a lower frequency signal acquisition rate. It can be interchanged with the use of PW Doppler and Color Doppler as necessary.

When an ultrasound scanner is used in a PW Doppler mode, it allows the operator to select a specific, small area on the image, and, in the tissue corresponding to that area, measure blood motion velocity. As part of this process, a gate is specified by the user, along an ultrasound beam line or direction (e.g., a one-dimensional signal is obtained). At the gate location, an algorithm is applied to process high-pass filtered, demodulated data into a Fourier transform, in order to look at low-frequency motion of structures, such as blood, within the gate. The result is a spectrum as a function of time that shows the general velocity at the gate location. Color doppler provides information about the presence or absence of flow, mean flow velocity and direction of flow within a selected color box on an anatomical feature. Spectral Doppler differs from Color Doppler imaging in that information is not obtained from the entire color box (as placed) but from a specified gate window, as noted above, a generally 2-4 mm wide sample volume.

Traditionally, ultrasound exams on vascular anatomy may include the steps of imaging a vessel in brightness mode (B-mode), then placing a Color box, then positioning a gate where an operator desires to measure Doppler velocity. These various steps are typically performed manually by the operator, in a way that is inefficient for the ultrasound operator.

One of the key drawbacks and limitation of Doppler is inconsistent placement of both gate and color box, where blood velocity is to be measured. Manual placement may be not only inefficient, as noted above, but vastly inconsistent between sonographers or even for the same sonographer, at different times. This variation may result in gathering less diagnostically useful information. In fact, even a slight offset in gate angle (also referred to as the "correction angle") can lead to up to 30% difference in accuracy of results. Generally, to evaluate an artery, the best angle for evaluation would be at zero degrees (parallel to the vessel) i.e. strongest signal and best waveforms would be at zero degrees. Zero degrees is not usually clinically feasible, however, so instead the probe is oriented at some angle between 0 (parallel) and 90 degrees (perpendicular) when evaluating the vessel (usually between 30 and 60 degrees).

By way of further background, to appreciate the criticality of accurate gate placement, it is to be understood that ultrasound systems calculate the velocity of blood flow according to the Doppler equation (the Fourier Transform):

$$\Delta f = \frac{2 f_0 \ V \cos \theta}{C},$$

where $\Delta f$ is the Doppler shift frequency, $f_0$ is the transmitted ultrasound frequency, $V$ is the velocity of reflectors (red blood cells), $\theta$ (theta, the Doppler gate angle) is the angle between the transmitted beam and the direction of blood flow within the blood vessel (the reflector path), and $C$ is the speed of sound in the tissue (1540 m/sec). Since the transmitted ultrasound frequency and the speed of sound in the tissue are assumed to be constant during the Doppler sampling, the Doppler shift frequency is directly proportional to the velocity of red blood cells and the cosine of the Doppler angle. The angle $\theta$ affects the detected Doppler frequencies. At a Doppler angle of 0°, the maximum Doppler shift will be achieved since the cosine of 0° is 1. Conversely, no Doppler shift (no flow) will be recorded if the Doppler angle is 90° since the cosine of 90° is 0.

The orientation of anatomical features and tissues through which blood flows (for example, carotid arteries) may vary from one patient to another; therefore, the operator is required to align the Doppler angle parallel to the vector of blood flow by applying the angle correction or angling the transducer. If the Doppler angle is small (<50°), this uncertainty leads to only a small error in the estimated velocity. If Doppler angles of 50° or greater are required, then precise adjustment of the angle correct cursor is crucial to avoid large errors in the estimated velocities. The Doppler angle should not exceed 60°, as measurements are likely to be inaccurate. For carotid arteries, a preferred angle of incidence is 45°±4. By way of example, in specific regard to carotid arteries, consistent use of a matching Doppler angle of incidence for velocity measurements in the common carotid artery and the internal carotid artery reduces errors in velocity measurements attributable to variation in $\theta$. It is known in the art that operator errors and inconsistencies have made this area of ultrasound technology a challenge.

Furthermore, the optimal position of a color box in a normal artery is in the mid lumen parallel to the vessel wall, whereas in a diseased vessel it should ideally be aligned parallel to the direction of blood flow. In the absence of plaque disease, the color box should generally not be placed on the sharp curves of a tortuous artery, as this may result in a falsely high velocity reading. If the color box is located too close to the vessel wall, artificial spectral broadening is inevitable. Leaving the specific positioning of the color box entirely to operator judgment can lead to unnecessary errors.

There it can be appreciated that is thus a need for improved ultrasound systems and methods for placing a gate and/or a color box during ultrasound imaging of any anatomical feature and tissue through which blood flows. The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate one or more of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

Figure 1:
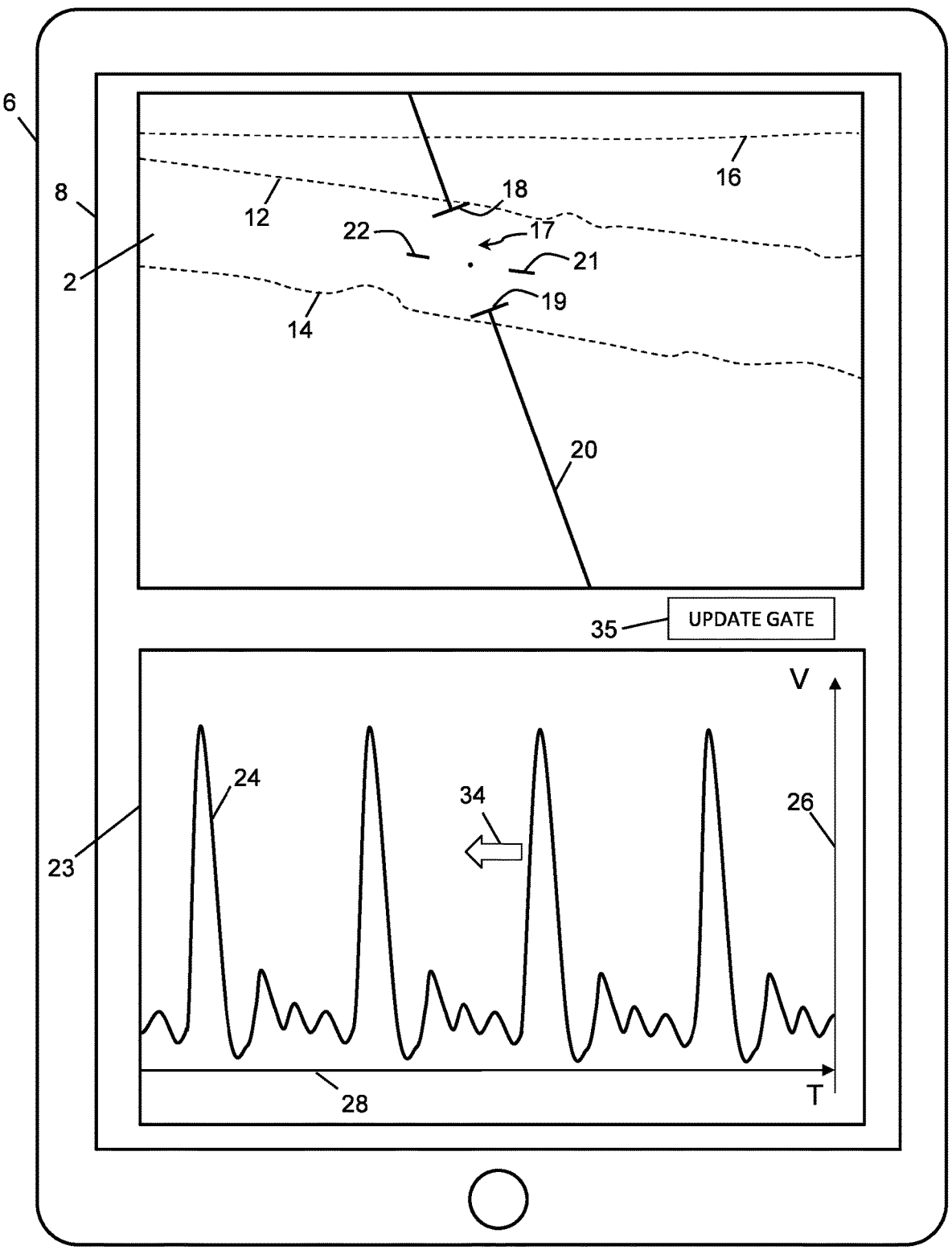
FIG. 1 is a user interface showing a B-mode image and a PW Doppler mode spectrum, according to an embodiment of the present invention.

Unless otherwise specifically noted, articles depicted in the drawings are not necessarily drawn to scale.

DETAILED DESCRIPTION

A. Exemplary Embodiments

The system of the present invention uses a transducer (a piezoelectric or capacitive device operable to convert between acoustic and electrical energy) to scan a planar region or a volume of an anatomical feature. Electrical and/or mechanical steering allows transmission and reception along different scan lines wherein any scan pattern may be used. Ultrasound data representing a plane or volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data is data which represents an anatomical feature sought to be assessed and reviewed by a sonographer.

In one embodiment there is provided a method and system for a trained AI model to position a gate, and wherein the system includes a spectral Doppler detector. In another embodiment there is provided a method and system for a trained AI model to position a color gate, and wherein the system includes a spectral Doppler detector. In another embodiment there is provided a method and system for a trained AI model to position both a gate and color box, and wherein the system includes a spectral Doppler detector.

At a high level, the present embodiments are generally directed to an automated way to position one or more of: a color box, a gate (e.g., a gate for PW Doppler imaging), correction angle and gate size on an ultrasound image. The embodiments automate the act of positioning the color box and PW gate parameters to remove the number of steps required to perform ultrasound examination of anatomical features and tissues through which blood flows. Since these various steps are typically performed manually by the operator, the present embodiments use these manual and other inputs to train an artificial intelligence (AI) model to learn the area on ultrasound images where these user interface items are placed, so as to predict the location automatically on subsequent new ultrasound image acquisitions.

The embodiments herein generally allow for the provision of ultrasound systems, ultrasound-based methods, computer-readable media storing computer-readable instructions, and portable computing devices for positioning a color box and/or a gate (including gate location, size and angle) on an ultrasound image of a feature of interest, for example arteries, for detecting medical conditions and anomalies therein.

Cerebrovascular disease (stroke) is the third leading cause of death in the United States, accounting for over 400,000 new cases diagnosed each year. Ultrasonography of the carotid arteries is the modality of choice for triage, diagnosis, and monitoring of cases of atheromatous disease. Important factors in diagnosis of atherosclerotic disease of the extracranial carotid arteries are the intima-media thickness, plaque morphology, criteria for grading stenosis, limiting factors such as the presence of dissection or cardiac abnormalities, distinction between near occlusion and total occlusion, and the presence of a subclavian steal. Challenges to the consistency of carotid ultrasound results may include poor Doppler technique including, as noted above, improper and inconsistent placement of the (Doppler) gate and/or the color box, even by experienced sonographers. These issues may be overcome within the scope of the present invention, by largely removing i) gate placement parameters and/or ii) color box location, orientation and size from a user/sonographer's control and instead employing one or more AI models trained to do so.

In one aspect, the present invention provides a method for positioning a gate on an ultrasound image generated during scanning of an anatomical feature using an ultrasound scanner, said gate at least defining an optimal location of a Doppler mode signal in a tissue, the method comprising deploying an artificial intelligence (AI) model to execute on a computing device communicably connected to the ultrasound scanner, wherein the AI model is trained so that when the AI model is deployed, the computing device generates a prediction of at least one of an optimal position, size, or angle for the gate on the ultrasound image generated during ultrasound scanning of the anatomical feature; acquiring, at the computing device, a new ultrasound image during ultrasound scanning; processing, using the AI model, the new ultrasound image to generate a prediction of one or more of an optimal gate position, size and angle (the "predicted optimized gate"); and employing the predicted optimized gate to enable corresponding Doppler mode signals.

In another aspect, the present invention provides A method for positioning a color box on an ultrasound image generated during ultrasound scanning of an anatomical feature, said color box at least defining an optimal location of a color Doppler mode signal in a tissue, the method comprising deploying an artificial intelligence (AI) model to execute on a computing device communicably connected to the ultrasound scanner, wherein the AI model is trained so that when the AI model is deployed, the computing device generates a prediction of optimal color box placement for the color box, on the ultrasound image, during ultrasound scanning of the anatomical feature; acquiring, at the computing device, a new ultrasound image during ultrasound scanning; processing, using the AI model, the new ultrasound image to generate a prediction of the optimal new color box position; and employing the new color box position to enable corresponding color Doppler mode signals.

In another aspect, the present invention provides the creation and deployment of an AI model which is trained to optimally place both a gate (position, size and angle) and color box on the ultrasound image generated during ultrasound scanning of an anatomical feature.

In still further aspects of the present invention, there are provided methods of training AI models, as described herein, to optimize their accuracy, in the placement of one or both of a gate (position, size and angle) and color box on the ultrasound image generated during ultrasound scanning of an anatomical feature.

In still further aspects of the present invention, there are provided a method of updating the gate (the previously set gate) as follows: displaying on a user interface of the computing device a live spectral Doppler mode ("SD-mode") ultrasound spectrum that corresponds to the predicted optimized gate; receiving input to update to a new predicted optimized gate; capturing a two-dimensional (2D) imaging mode ("2D mode") ultrasound image ("captured image"); applying the AI model to the captured image to generate a prediction of one or more of an optimal updated gate position, size and angle (the "updated optimized gate"); employing the updated optimized gate to enable corresponding SD-mode signals; and displaying a live-SD mode ultrasound spectrum that corresponds to the updated optimized gate.

It is to be understood that "feature" (used interchangeably herein with "anatomical feature") as used herein and to which the gate and color box placement embodiments of the invention may be applied, (for example, the methods, processes and systems described herein), is, broadly and without limitation, any anatomical feature and tissue through which blood flows and in which measurement of blood flow is desired. As such, "feature" comprises the vascular system and the cardiovascular system. With the vascular system, arteries include, but are not limited to the group consisting of carotid artery, subclavian artery, axillary artery, brachial artery, radial artery, ulnar artery, aorta, hypergastic artery, external iliac artery, femoral artery, popliteal artery, anterior tibial artery, arteria dorsalis celiac artery, cystic artery, common hepatic artery (hepatic artery proper, gastric duodenal artery, right gastric artery), right gastroepiploic artery, superior pancreaticoduodenal artery, inferior pancreaticoduodenal artery, pedis artery, posterior tibial artery, ophthalmic artery and retinal artery. Within the cardiovascular system, "feature" includes but is not limited to the heart (including fetal heart) and gate placement in or around heart valves. The term "feature" additionally comprises an umbilical cord.

Referring to FIG. 1, an example display device 6 (e.g., a tablet computer, smartphone, or the like, which may be communicably coupled to an ultrasound scanner), with screen 8 is shown on which a B-mode image 2 is displayed. The B-mode image 2 includes features of a body, such as blood vessel walls 12, 14 and skin 16. Also displayed on the B-mode image 2 is a gate 17 that indicates where a Doppler mode signal in the tissue corresponding to the gate location is obtained. The extent of the gate 17 is defined by ends 18, 19, and the direction of the gate 17 is defined by line 20.

Typically, the blood vessel under observation is not in line with the ultrasound line, and so additional lines next to the gate are shown to indicate a correction angle for the PW Doppler signal. The additional lines should generally be positioned parallel to the vessel walls. The ideal Doppler signal is parallel with the blood flow, and, at the other extreme, a Doppler signal is unobtainable if the blood flow is entirely perpendicular to the ultrasound line. The position and angle of the gate can be adjusted to best orient for the particular ultrasound image, and the correction angle (also referred to as gate angle herein) can be set to provide additional information to the system about the angle of the vessel side walls, so that the Doppler signal can be corrected accordingly. In FIG. 1, the correction lines 21, 22 are shown positioned parallel to the walls 12, 14 of the blood vessel being scanned.

Also displayed on the touchscreen 8 is a Doppler mode display portion 23, which shows a corresponding Doppler mode spectrum 24 that represents velocity of blood flow on vertical axis 26 versus time on horizontal axis 28. The displayed spectrum 24 moves to the left of the Doppler mode display portion 23 as time progresses, in the direction of block arrow 34. The user interface of FIG. 1 is shown as an example only, and other configurations of user interface items may be possible in different embodiments.

Traditionally, the placement of the gate 17 on the B-mode image 2 is performed manually, along with manual inputs to resize the ends 18, 19 of the gate, as well the correction lines 21, 22 specifying the correction angle. Modifying these various user interface items to obtain the desired Doppler signal to be displayed (e.g., in the display portion 23) may take time. In certain instances, the operator may also need to re-adjust these items to optimize the Doppler signal to be displayed.

Additionally shown on the user interface of FIG. 1 is Update Gate button 35, which enables a user to provide input to direct the AI model to generate a prediction of one or more of an optimal updated gate position, size and angle (the "updated optimized gate"). Such an updating feature is described in further detail below and specifically in FIGS. 12-14.

Figure 2:
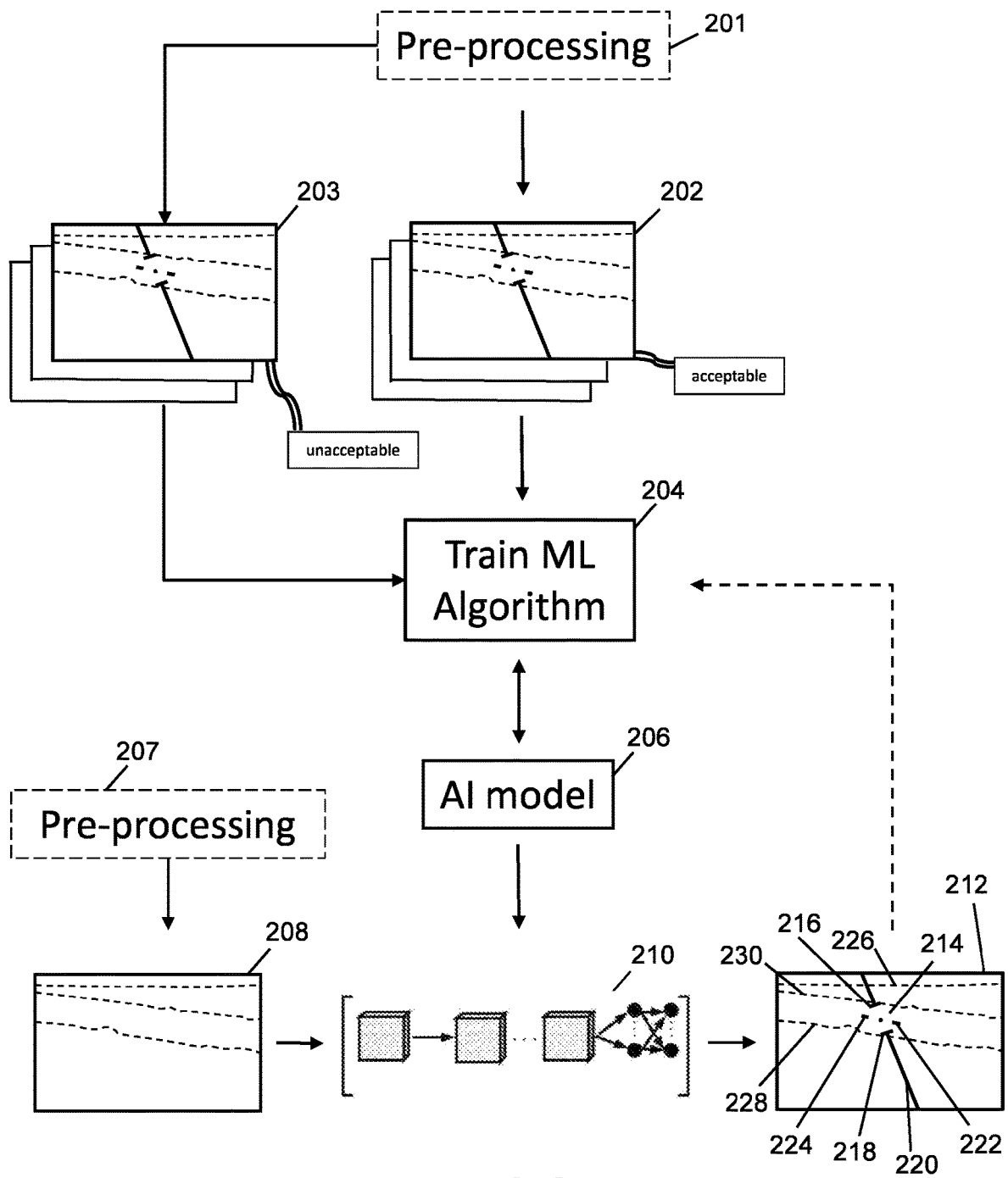
FIG. 2 is a diagram of a method for training and deployment of an AI model for placement of a gate during ultrasound imaging, according to an embodiment of the present invention.

Referring to FIG. 2, shown there is a diagram of a method for training and deployment of an AI model for placement of a gate during ultrasound imaging, according to an embodiment of the present invention. Generally, a software module may be provided on the display device 6 that runs in parallel to standard ultrasound imaging software used to receive inputs from the operator and display live ultrasound images to the user. This software module may track where a gate is manually placed by an operator when in PW Doppler mode. Along with the gate position, it may also track the gate size, and/or correction angle when it is positioned on the B-mode image.

As shown in FIG. 2, these various inputs are shown generally as ultrasound images 202 and 203 which includes the underlying B-mode image, along with a manually-inputted gate position, gate size, and the correction angle. It is to be understood that the inputs for training step 204 need not be B-mode images and may in fact be Doppler images as well. These various user inputs may be collected as a "snapshot" of the settings used by the ultrasound imaging system for generating the Doppler imagine desired by the operator. In some embodiments, these various inputs may be collected as training data each time the user changes the gate attributes. In some embodiments, a timer can be set so that the snapshot of these various inputs is only treated as training data if they are not immediately changed again within some set time period (e.g., 0.25-2 seconds). In this latter scenario, the lack of change in the inputs after the predetermined period of time likely means that the user has finalized the input for visualizing the Doppler data, so that these inputs are more likely to be accurate and therefore useful as training data.

The training ultrasound frames (202-203), which may be B-mode or Doppler images may include ultrasound frames labeled as Acceptable with gate parameters that are tagged as acceptable and representative of an optimal gate location and/or size and/or angle and ultrasound frames labeled as Unacceptable that are tagged respectively as unacceptable and unrepresentative of an optimal gate location and/or size and/or angle. Both the training ultrasound frames labeled as Acceptable and Unacceptable may themselves be used for training and/or reinforcing AI model 206. This is shown in FIG. 2 with tracking lines from ultrasound images labeled as both Acceptable and Unacceptable, to training algorithm step 204.

In some embodiments, an optional pre-processing act 201 may be performed on the underlying ultrasound image frames 202 and 203 to facilitate improved performance and/or accuracy when training the machine learning (ML) algorithm. For example, it may be possible to pre-process the ultrasound images 202 and 203 through a high contrast filter to reduce the granularity of greyscale on the ultrasound images 202 and 203.

Additionally, or alternatively, it may be possible to reduce scale of the ultrasound images 202-203 prior to providing the ultrasound images 202-203 to the training algorithm step 204. Reducing the scale of ultrasound images 202-203 as a preprocessing step may reduce the amount of image data to be processed during the training act 204, and thus may reduce the corresponding computing resources required for the training act 204 and/or improve the speed of the training act 204.

Various additional or alternative pre-processing acts may be performed in act 201. For example, these acts may include data normalization to ensure that the various ultrasound frames 202-203 used for training have generally the same dimensions and parameters.

In act 204, the various inputs on the training ultrasound data 202 and 203 are provided as labeled data for use in training a machine learning (ML) algorithm. For example, the various training data 202 and 203 may be inputted into a deep neural network that can learn how to correctly predict a gate position, gate width, and/or correction angle on new ultrasound images.

The result of the training may be the AI model 206, which represents the mathematical weights and/or parameters learned by the deep neural network to predict an accurate gate position, width, and/or correction angle on new ultrasound images. The training act 204 may involve various additional acts (not shown) to generate a suitable AI model 206. For example, these various deep learning techniques include regression, classification, feature extraction, and the like. Any generated AI models may be iteratively tested to ensure they are not overfitted and sufficiently generalized for identifying gate position, width, and/or correction angle on new ultrasound images. In various embodiments, the machine learning may be supervised or unsupervised.

For example, in some embodiments, once the training images 202 and 203 are obtained with tracked input for gate position, width, and/or correction angle (e.g., the labeled data for training), a deep neural network may use them as inputs and the associated expert details of the gate position, width, and/or correction angle as desired may be outputted to determine value sets of neural network parameters defining the neural networks.

In some embodiments, the various user interface elements associated with the gate position, gate width, and/or correction angle may form a mask on the underlying B-mode image. In some embodiments, the neural network may be configured to receive one or more ultrasound images as input and to have a softmax layer as an output layer. The output layer may specify whether the corresponding pixels of the underlying B-mode image form part of the user interface elements for specifying the gate location, gate width, and/or correction angle (e.g., whether the corresponding pixels form the various user interface elements 17, 18, 19, 20, 21, 22 discussed above with respect to FIG. 1).

In some embodiments, the training images file may include an image identifier field for storing a unique identifier for identifying the underlying B-mode image, and a segmentation mask field for storing an identifier for specifying the user interface elements representing the gate location, gate width, and/or correction angle inputted by an operator.

In some embodiments, using a cross-validation method on the training process would optimize neural network hyper-parameters to try to ensure that the neural network can sufficiently learn the distribution of all possible details for the gate position, width, and/or correction angle without overfitting to the training data. In some embodiments, after finalizing the neural network architecture, the neural network may be trained on all of the data available in the training image files.

In various embodiments, batch training may be used and each batch may consist of multiple images, thirty-two for example, wherein each example image may be scaled to be gray-scale, 256*256 pixels, without any preprocessing applied to it.

In some embodiments, the deep neural network parameters may be optimized using the Adam optimizer with hyper-parameters as suggested by Kingma, D. P., Ba, J. L.: Adam: a Method for Stochastic Optimization, International Conference on Learning Representations 2015 pp. 1-15 (2015), the entire contents of which are incorporated here-with. The weight of the convolutional layers may be initialized randomly from a zero-mean Gaussian distribution. In some embodiments, the Keras™ deep learning library with TensorFlow™ backend may be used to train and test the models.

In some embodiments, during training, different steps may be taken to stabilize learning and prevent the model from over-fitting. Using the regularization method, e.g., adding a penalty term to the loss function, has made it possible to prevent the coefficients or weights from getting too large. Another method to tackle the over-fitting problem is dropout. Dropout layers limit the co-adaptation of the feature extracting blocks by removing some random units from the neurons in the previous layer of the neural network based on the probability parameter of the dropout layer. Moreover, this approach forces the neurons to follow overall behaviour. This implies that removing the units would result in a change in the neural network architecture in each training step. In other words, a dropout layer performs similar to adding random noise to hidden layers of the model. A dropout layer with the dropout probability of 0.5 may be used after the pooling layers.

Data augmentation is another approach to prevent over-fitting and add more transitional invariance to the model. Therefore, in some embodiments, the training images may be augmented on-the-fly while training. In every mini-batch, each sample may be translated horizontally and vertically, rotated and/or zoomed, for example. The present invention is not intended to be limited to any one particular form of data augmentation, in training the AI model. As such, any mode of data augmentation which enhances the size and quality of the data set, and applies random transformations which do not change the appropriateness of the label assignments may be employed, including but not limited to image flipping, rotation, translations, zooming, skewing, and elastic deformations.

Referring still to FIG. 2, after training has been completed, the sets of parameters stored in the storage memory may represent a trained neural network for masking out the user interface elements corresponding to the gate location, size, and/or correction angle.

In order to assess the performance of the model, the stored model parameter values can be retrieved any time to perform image assessment through applying an image to the neural networks represented thereby.

In some embodiments, the deep neural network may include various layers such as convolutional layers, max-pooling layers, and fully connected layers. In some embodiments, the final layers may include a softmax layer as an output layer having outputs which eventually would demonstrate respective determinations that an input set of pixels form part of the user interface elements corresponding to the gate location, size and/or correction angle. Accordingly, in some embodiments, the neural network may take at least one image as an input and output a binary mask indicating which pixels belong to the user interface elements corresponding to the gate location, size, and/or correction angle (e.g., the AI model classifies which area each pixel belongs to).

To increase the robustness of the AI model 206, in some embodiments, a broad set of training data may be used at act 204. For example, it is desired that ultrasound images of a plurality of anatomical features (for example a variety of arteries), both transverse and longitudinally, and at differing frequencies, depths and gains be included in the training ultrasound images 202 and 203.

More specifically, training medical images 202 and 203 may be labeled with one or more features associated with/ are hallmarks of an optimal gate placement. This may include identifying a variety of features visualized in the captured training medical image including but not limited to vessel walls, skin and other relevant and proximal anatomical landmarks. In at least some embodiments, this data may be received from trainer/user input. For example, a trainer/user may label the features relevant for the application visualized in each training image.

The image labelling can be performed, for example, by a trainer/user observing the training ultrasound images, via a display screen of a computing device, and manually annotating the image via a user interface. In some aspects, the training ultrasound images used for the method herein will only be images in which the image quality is of a sufficient quality threshold to allow for proper, accurate and optimal gate placement. For example, this can include training ultrasound images having a quality ranging from a minimum quality in which target features are just barely visible for labelling (e.g., annotating), to excellent quality images in which the target features are easily identifiable. In various embodiments, the training medical images can have different degrees of images brightness, speckle measurement and SNR. Accordingly, training ultrasound images 202 and 203 can include a graduation of training medical images ranging from images with just sufficient image quality to high image quality. In this manner, the machine learning model may be trained to identify features on training medical images that have varying levels of sufficient image quality for later interpretation and probability assessment.

As noted above, there are optimal angles for acquiring ultrasound mages of anatomical features such as blood vessels (hence the need for gate placement). However, unskilled or novice ultrasound operators may not have developed the skillset to achieve this. Thus, training AI model 206, with off-angle ultrasound images may increase the robustness of the model, so as to be operational and accurate when new ultrasound images are acquired by unskilled or novice operators. This is compounded by the fact that AI model 206 may be trained on a plurality of different like features, with differing characteristics, in varying locations in the body.

Overall, the scope of the invention and accorded claims are not intended to be limited to any one particular process of training AI model 206. Such examples are provided herein by way of example only. AI model 206 may be trained by both supervised and unsupervised learning approaches at 204 although due to scalability, unsupervised learning approaches, which are well known in the art, are preferred. Other approaches may be employed to strengthen AI model 206.

Figure 11:
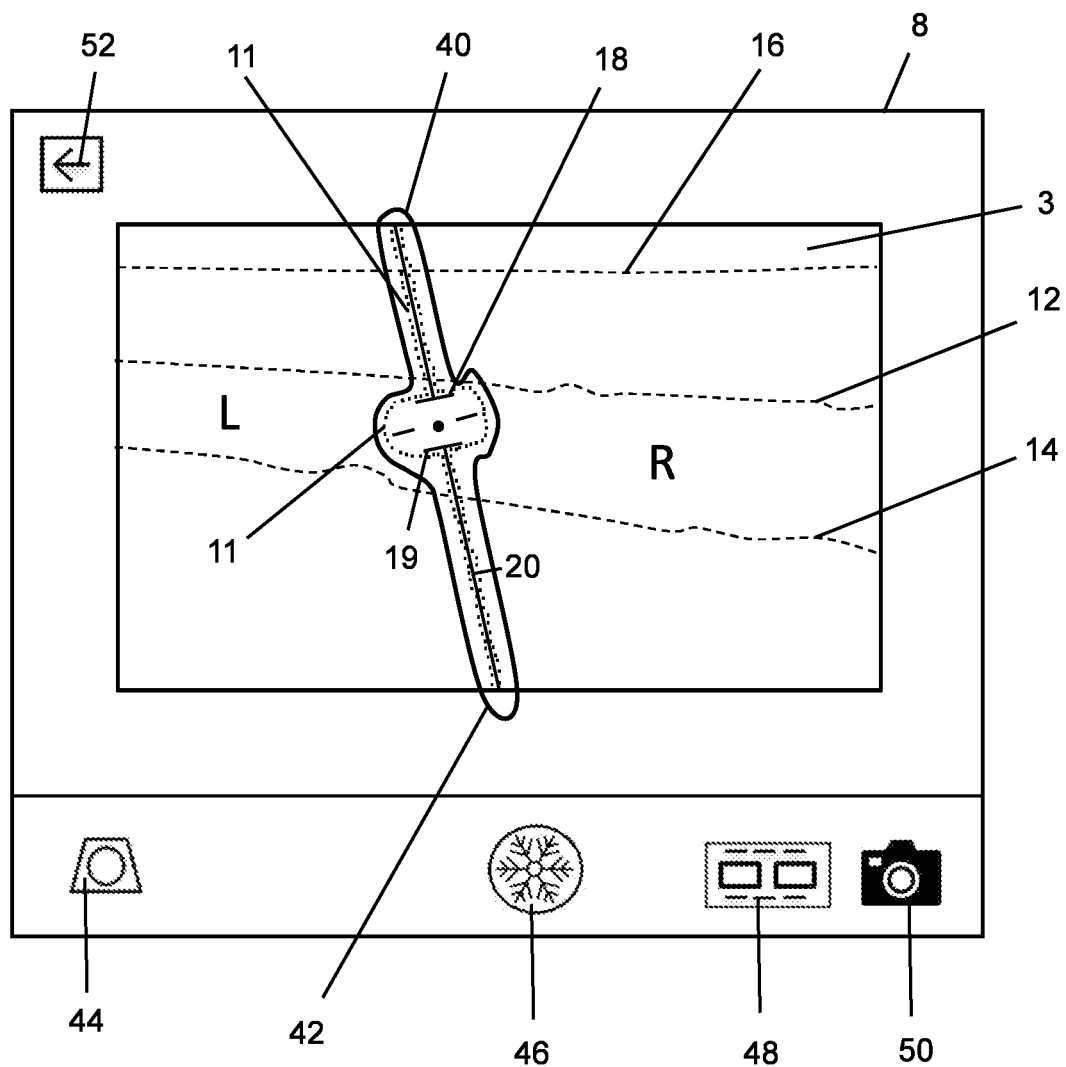
FIG. 11 is a is a schematic diagram of a vascular image (Doppler ultrasound) showing labeled boundaries (two masks) for identifying, labeling and training a gate on an AI model, according to an embodiment of the present invention.

For example, unique to Doppler imaging, AI model 206 may be trained with a plurality of training ultrasound frames, each of said training ultrasound frames comprising a mask of an optimal gate (location and/or size and/or angle) created in Doppler mode, from a plurality of manual inputs, said manual inputs defining a labeled mask of optimal gate parameters. Referring to FIG. 11, screen 8 is shown on which an ultrasound image in color Doppler mode 3 is displayed. The ultrasound image in color Doppler mode 3 includes features of a body, such as blood vessel walls 12, 14 and skin 16. Also displayed on the ultrasound image 3 is a gate 17 that indicates where a Doppler mode signal in the tissue corresponding to the gate location is obtained. The extent of the gate 17 is defined by ends 18, 19, and the direction of the gate 17 is defined by line 20. Gate boundary points (11) are placed around gate 17 delineating the gate from other non-gate image areas (mask 40). More specifically, image areas that are on the right side "R" of gate boundary points 11 may be removed prior to labeling such images as acceptable (A) for training AI model 206 or 622. Likewise, image areas that are on the left side "L" of the gate boundary points 11 that are on each side of may be removed prior to labeling such images as acceptable (A) for training AI model 206 or 622. Further illustrated in FIG. 11, in respect to screen 8 are exemplary user experience/interaction features such as color Doppler mode visual indicator 44, freeze screen contact point 46, film contact point 48, photo capture contact point 50 and return to previous screen contact point 52. It is to be understood that these and any other contact points on a user interface described herein may be via a button, a touch-sensitive region of the user interface, a dial, a slider, a drag gesture, a voice command, a keyboard, a mouse, a trackpad, a touchpad, or any combination thereof.

Referring back to FIG. 2, once a satisfactory AI model 206 is generated, the AI model 206 may be deployed for execution on a neural network 210 to predict the characteristics of the gates on new ultrasound images 208. Notably, the neural network 210 is shown in FIG. 2 for illustration as a convolution neural network-which may have various nodes in the input layer, hidden layers, and output layers. However, in various embodiments, different arrangements of the neural network 210 may be possible.

In various embodiments, prior to being processed for assessment of predicted optimal gate parameters, the new ultrasound images 208 may optionally be pre-processed. This is shown in FIG. 2 with the pre-processing act 207 in dotted outline. In some embodiments, these pre-processing acts 207 may be analogous to the pre-processing acts 201 performed on the training ultrasound frames 202 and 203 (e.g., processing through a high contrast filter and/or scaling), to better align the new ultrasound images 208 with the training ultrasound images 202 and 203, and thereby facilitate improved accuracy in predicting optimal gate parameters. For example, pre-processing an input image may help standardize the input image so that it matches the format (e.g., having generally the same dimensions and parameters) of the training ultrasound images 202 and 203 that the AI machine model 206 is trained on.

In various embodiments, the new ultrasound images 208 may be live images acquired by an ultrasound imaging system (e.g., the system discussed with respect to FIGS. 4 and 5 below). For example, the AI model 206 may be deployed for execution on the scanner 412 and/or the display device 6 discussed in more detail below. Additionally, or alternatively, the AI model 206 may be executed on stored (as opposed to new) ultrasound images that were previously acquired (e.g., as may be stored on a Picturing Archiving and Communication System (PACS)).

Whether the images are stored ultrasound images or new ultrasound images 208, the AI model 206 enables the neural network 210 to generate a prediction of optimal gate parameters (one or more of gate location, gate size and gate angle) depicted then in ultrasound image frames 212. Further illustrated in ultrasound image frames 212 are features of a body, such as blood vessel walls 228 and 230 and skin 226. Also displayed on the ultrasound images 212 is a gate 214 that indicates where a Doppler mode signal in the tissue corresponding to the gate location is obtained. The extent of the gate 214 is defined by ends 216 and 218, and the direction of the gate 214 is defined by line 220. Correction lines 222 and 224 are shown positioned parallel to the walls 228 and 230 of the blood vessel being scanned.

When executed in this manner, the AI model 206 may allow the neural network 210 to predict the position, size, and/or correction angle of gate to be placed on the new ultrasound frames 208, resulting in corresponding ultrasound frames 212 with a predicted position, size, and/or correction of the gate. The predicted characteristics of the gate may then be used for input to the ultrasound scanner to acquire Doppler signals. For example, the predicted characteristics of the gate may be interpreted by the ultrasound system as if the predicted gate location, size, and/or correction angle were manually-inputted user interface manipulations of an operator.

In some embodiments, the ultrasound system may be configured to apply the AI model 206 periodically (e.g., in regular intervals of between 1-4 seconds) to automatically optimally position and update position for gate position, size and/or correction angle.

An ultrasound scanner may generally transmit and receive ultrasound signals according to an ultrasound sequence when generating the live ultrasound image feed (e.g., the sequence and characteristics in which ultrasound pulses are directed to the tissue and the resultant echo signals received). Manual modification of the gate characteristics generally results in an update of the ultrasound sequence used to acquire ultrasound signals.

However, gate characteristics predicted by the AI model 206 may not always be suitable for updating the ultrasound sequence. As such, in some embodiments, the sequence may only be updated if the output of the AI model 206 is of a high enough confidence level (e.g., 70%) and/or if one or more of the gate position, size, and/or correction angle has changed (e.g., moved or adjusted) beyond a threshold amount (e.g., 10-40%). This may reduce the constant updating of the ultrasound sequence that might otherwise occur, and the resulting associated jumping or flickering in the ultrasound images being displayed.

Referring still to FIG. 2, in some embodiments, the ultrasound frames 212 with predicted gate characteristics may optionally themselves be used for training and/or reinforcing the AI model 206. This is shown in FIG. 2 with a dotted line from the ultrasound frames 212 with the predicted gate characteristics being provided to the training act 204. For example, the transmission of such reinforcement training ultrasound data may be sent to a centralized server 520 which collects various predicted gate characteristics for updating the AI model 206, using the distributed network 500 discussed in greater detail below with respect to FIG. 5.

Figure 3:
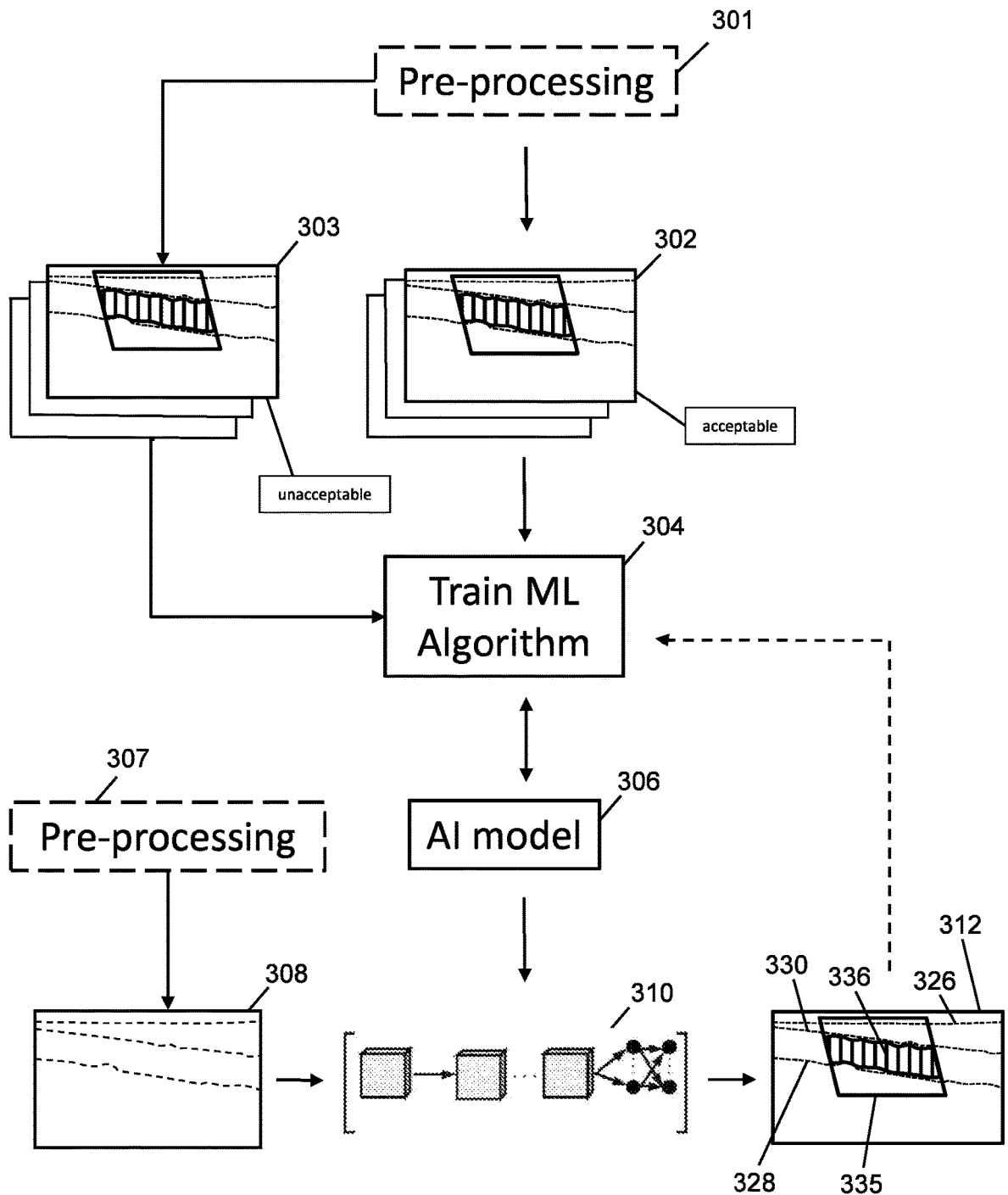
FIG. 3 is a diagram of a method for training and deployment of an AI model for placement of a color box during ultrasound imaging, according to an embodiment of the present invention.

Referring to FIG. 3, shown there is a diagram of a method for training and deployment of an AI model for placement of a color box during ultrasound imaging, according to an embodiment of the present invention. The elements of FIG. 3 generally correspond to those in FIG. 2, except instead of training an AI model 206 for placement of gate position, size, and/or correction angle, FIG. 3 is directed to training an AI model 306 for placement of a color box. The techniques, processes, and variations discussed above with respect to FIG. 2 may thus generally be applicable to FIG. 3 also.

Generally, when an ultrasound system is configured to be in Color Doppler mode, the operator is required to place a color box in the user interface for identifying the corresponding tissue in which the color mode signal is obtained and displayed. For example, the color box may be shown as an angled box (e.g., parallelogram), as is illustrated in the ultrasound images 302 in FIG. 3.

The training ultrasound frames (302-303), which as above in regard to FIG. 2 may be B-mode or Doppler images, includes ultrasound frames labeled as Acceptable with color box placements that are tagged as acceptable and representative of an optimal color box location and size and may include ultrasound frames labeled as Unacceptable that are tagged respectively as unacceptable and unrepresentative of an optimal color box gate location and size. Both the training ultrasound frames labeled as Acceptable and Unacceptable may themselves be used for training and/or reinforcing AI model 306. This is shown in FIG. 3 with tracking lines from ultrasound images labeled as both Acceptable and Unacceptable, to training algorithm step 304.

In some embodiments, an optional pre-processing act 301 may be performed on the underlying ultrasound image frames 302 and 303 to facilitate improved performance and/or accuracy when training the machine learning (ML) algorithm. For example, it may be possible to pre-process the ultrasound images 302 and 303 through a high contrast filter to reduce the granularity of greyscale on the ultrasound images 302 and 303.

Additionally, or alternatively, it may be possible to reduce scale of the ultrasound images 302-303 prior to providing the ultrasound images 302-303 to the training algorithm step 304. Reducing the scale of ultrasound images 302-303 as a preprocessing step may reduce the amount of image data to be processed during the training act 304, and thus may reduce the corresponding computing resources required for the training act 304 and/or improve the speed of the training act 304.

Various additional or alternative pre-processing acts may be performed in act 301. For example, these acts may include data normalization to ensure that the various ultrasound frames 302-303 used for training have generally the same dimensions and parameters.

In act 304, the various inputs on the training ultrasound data 302 and 303 are provided as labeled data for use in training a machine learning (ML) algorithm. For example, the various training data 302 and 303 may be inputted into a deep neural network 310 that can learn how to correctly predict a color box placement/location and size on new ultrasound images of vascular features as shown in ultrasound images 312.

As such, once the ML algorithm is trained using the various techniques discussed above, an AI model 306 may be developed and the AI model 306 may be deployed into a neural network 310. When new ultrasound images 308 (optionally preprocessed at act 307) are fed into the neural network 310 configured with AI model 306, it may be able to predict the optimal position for the placement of the color box as shown on ultrasound images 312.

Further illustrated in ultrasound image frames 312 in FIG. 3 are features of a body, such as blood vessel walls 328 and 330 and skin 326. Also displayed on the ultrasound images 312 is a color box 335, along with striated markers of the insonation angle 336. This the angle between the path of the Doppler pulses and the direction of flow in the vascular feature as indicated by the orientation of the color box. As noted above, when this angle is 90° (top), there will be no frequency shift because cos (90°)=0. With angle correction in any vascular feature, more of the flow becomes detectable.

The present embodiments may be deployed in various example scenarios. Also, variations to the embodiments described herein may be possible.

For example, as discussed herein, the AI model 206 for predicting gate location/size/correction angle (FIG. 2) and the AI model 306 for predicting color box location (FIG. 3) have been described as separate AI models. However, in various embodiments, the two may be combined into a single AI model that takes both the training inputs 202, 302 discussed in FIGS. 2 and 3 and generates a single AI model for predicting both gate size/location/correction angle and color box location. An illustration of this single but combined function AI model is illustrated more fully in FIG. 6.

Figure 6:
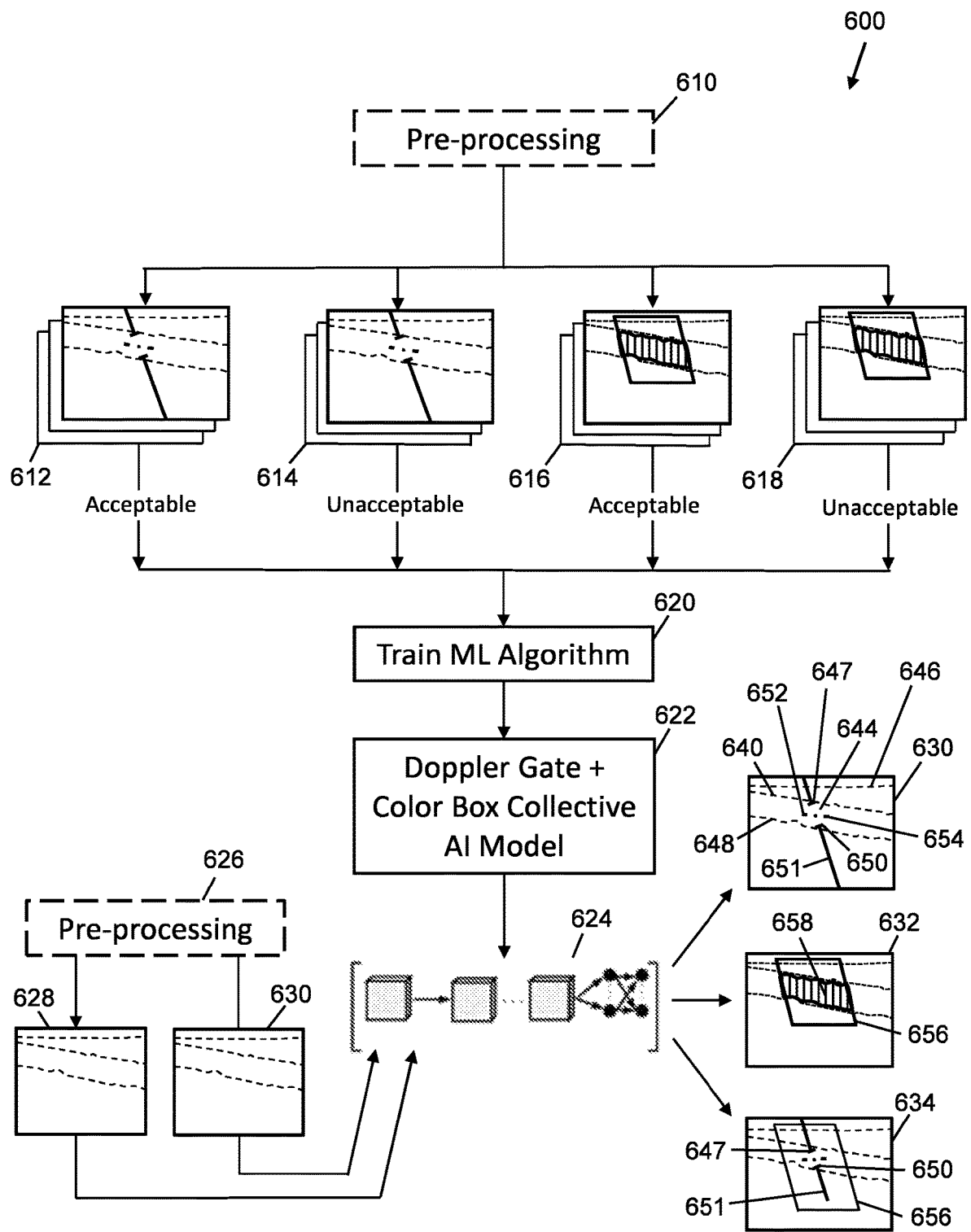
FIG. 6 is a diagram of a method for training and deployment of an AI model for both the placement of a gate and a color box during ultrasound imaging, according to an embodiment of the present invention.

Referring to FIG. 6, shown there is a diagram of a method 600 for training and deployment of a dual AI model for i) placement of gate (location, size, and/or correction angle); and ii) placement of a color box during ultrasound imaging of a vascular feature, according to an embodiment of the present invention. The elements of FIG. 6 generally correspond to those respectively in FIGS. 2 and 3, except instead of training an AI model 206/306 for singular placement of gate position, size, and/or correction angle or color box, FIG. 6 is directed to training a dual function AI model 622 for both placement of gate (location, size, and/or correction angle) and placement of a color box during ultrasound imaging of a vascular feature. The techniques, processes, and variations discussed above with respect to FIGS. 2 and 3 may thus generally be applicable to FIG. 6 also.

The training ultrasound frames (612, 614, 616 and 618), which as above regarding FIGS. 2 and 3 may be B-mode ultrasound images or Doppler mode images, include ultrasound frames labeled as Acceptable (for example 612) with gate parameters that are tagged as acceptable and representative of an optimal gate location and/or size and/or angle and ultrasound frames labeled as Unacceptable (for example 614) that are tagged respectively as unacceptable and unrepresentative of an optimal gate location and/or size and/or angle. Ultrasound frames labeled as Acceptable (for example 616) with color box location and size which are tagged as acceptable and representative of an optimal color box location and size and ultrasound frames labeled as Unacceptable (for example 614) with color box location and size which are tagged respectively as unacceptable and unrepresentative of an optimal color box location and size. Both the training ultrasound frames labeled as Acceptable and Unacceptable may themselves be used for training and/or reinforcing Doppler gate and color box collective AI model 622. This is shown in FIG. 6 with tracking lines from ultrasound images labeled as both Acceptable and Unacceptable, to training algorithm step 620.

In some embodiments, an optional pre-processing act 610 may be performed on the underlying ultrasound image frames 612-618 to facilitate improved performance and/or accuracy when training the machine learning (ML) algorithm. For example, it may be possible to pre-process the ultrasound images 612-618 through a high contrast filter to reduce the granularity of greyscale on the ultrasound images 612-618.

Additionally, or alternatively, it may be possible to reduce scale of the ultrasound images 302-303 prior to providing the ultrasound images 612-618 to the training algorithm step 620. Reducing the scale of ultrasound images 612-618 as a preprocessing step may reduce the amount of image data to be processed during the training act 620, and thus may reduce the corresponding computing resources required for the training act 620 and/or improve the speed of the training act 620.

Various additional or alternative pre-processing acts may be performed in act 620. For example, these acts may include data normalization to ensure that the various ultrasound frames 612-618 used for training have generally the same dimensions and parameters.

In act 620, the various inputs on the training ultrasound data 612-618 are provided as labeled data for use in training a machine learning (ML) algorithm. For example, the various training data 612-618 may be inputted into a deep neural network 624 that can learn how to correctly predict both optimal gate parameters and optimal color box placement/location and size on new ultrasound images of vascular features as shown in ultrasound images 630 (AI model predicted placement of gate alone), 632 (AI model predicted placement of color box alone), and 634 (AI model predicted placement of both optimal gate parameters and optimal color box placement/location and size.

As such, once the ML algorithm is trained using the various techniques discussed above, an AI model 622 may be developed and the AI model 622 may be deployed into a neural network 624. When new ultrasound images 628 and 630, for example, (optionally preprocessed at act 626) are fed into the neural network 624 configured with AI model 622, it may be able to predict i) optimal gate parameters (image 630); ii) optimal color box placement/location and size (image 632) and iii) both optimal gate parameters and optimal color box placement/location and size (image 634).

Further illustrated in ultrasound image frames 630-634 in FIG. 6 are features of a body, such as blood vessel walls 640 and 648 and skin 646. Also displayed on the ultrasound images 630 and 634 is a gate 644 that indicates where a Doppler mode signal in the tissue corresponding to the gate location is obtained. The extent of the gate 644 is defined by ends 647 and 650, and the direction of the gate 644 is defined by line 651. Correction lines 652 and 654 are shown positioned parallel to the walls 640 and 648 of the blood vessel being scanned. Also displayed on the ultrasound images 632 and 634 is a color box 656 along with striated markers of the insonation angle 658.

In various embodiments, the embodiments described above for predicting color box may be used in Color Doppler modes and/or Power Doppler modes.

In various embodiments, the placement of a gate may be performed in either mono mode (e.g., mono PW Doppler mode, where only PW samplings are obtained and the B-mode is turned off but B-mode can be manually toggled on by the operator when desired); or duplex mode (where multiple types of ultrasound signals are interleaved to generate a live ultrasound image with multiple types of data together). An example of duplex scanning is B-mode ultrasound signals and PW ultrasound signals being interleaved together to provide a live B-mode image of structure being imaged and also PW Doppler data where the gate is placed. The embodiments of FIG. 2 may be employed in this instance. Another example of duplex scanning is B-mode/Color Doppler, where the embodiments of FIG. 3 may be employed.

Additionally or alternatively, FIG. 2 has generally been illustrated in relation to placement of a gate on a simple B-mode image with no other modes activated, and FIG. 3 has similarly been illustrated in relation to placement of a color box on a simple B-mode image with no other modes activated. However, in some embodiments, both a color box and a gate may be present on a B-mode image. This may be the case in certain ultrasound systems that allow for three different imaging modes to be combined together. Examples of these include adding a further mode to the duplex B/PW combination already discussed: e.g., adding a Color Doppler or Power Doppler mode. This results in additional combination modes that combine: B-mode, PW Doppler, and Color Doppler together (B/PW/Color); or B-mode, PW Doppler, and Power Doppler together (B/PW/Power). In these triplex modes, the AI model(s) discussed herein may be used together to predict both the gate characteristics for PW Doppler, and a color box for Color Doppler or Power Doppler.

Moreover, while the placement of a gate in relation to FIG. 2 above has generally been in relation to a spectral Doppler mode, in various embodiments, it may be possible to use the embodiments of FIG. 2 in imaging modes that do not involve spectral Doppler at all. For example, the embodiments described herein may generally be used to predict gate characteristics (e.g., location). As such, the present embodiments may be employed in any ultrasound imaging mode that traditionally requires manual input of a gate.

For example, M-Mode (e.g., Motion-mode) provides a time motion display of ultrasound signals along a chosen ultrasound line. The embodiments of FIG. 2 may be employed to learn and predict the positioning of a gate in M-mode.

In another example, some ultrasound systems have elastography modes that provide a map and/or measurement of tissue stiffness (e.g., using shear wave vibrations and/or acoustic radiation force imaging (ARFI)). In these modes, a region of tissue may be continuously measured with outputs being displayed in real-time to the user. In order to achieve proper targeting within the tissue, it may be helpful to provide a "gate" to position the desired elastography measurement area. The systems and methods described herein may be used in these elastography modes to predict positioning of the gate for live elastography measurements.

Figure 4:
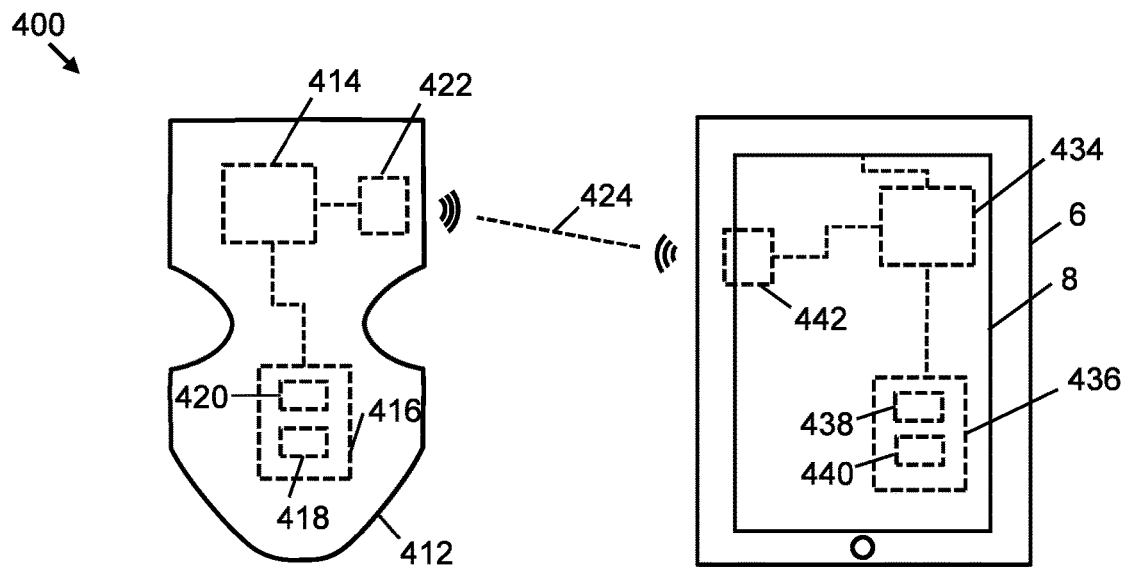
FIG. 4 is a schematic diagram of an ultrasound imaging system according to an embodiment of the present invention.

Referring to FIG. 4, an exemplary system 400 on which the present embodiments may be practised is shown. The system 400 may include ultrasound scanner 412 (referred to herein as "scanner" for brevity) that acquires the ultrasound imaging frames 2, 202, 302 (shown in FIGS. 1, 2, and 3 above) and which the placement of the gate or color box would result in acquisition of corresponding ultrasound signals (e.g., Doppler signals). The system 400 may include an ultrasound scanner 412 with a processor 414, which may be connected to a non-transitory computer readable memory 416 storing computer readable instructions 418, which, when executed by the processor 414, may cause the scanner 412 to provide one or more of the functions of the system 400. Such functions may be, for example, the acquisition of ultrasound data, the processing of ultrasound data, the scan conversion of ultrasound data, the transmission of ultrasound data or images to a display device 6, the detection of operator inputs to the scanner 412, and/or the switching of the settings of the scanner 412 (e.g., to update the ultrasound sequence to acquire Doppler signals in area represented by the gate position, gate width, correction angle and/or color box, as predicted by AI models 206, 306).

Also stored in the computer readable memory 416 may be computer readable data 420, which may be used by the processor 414 in conjunction with the computer readable instructions 418 to provide the functions of the system 400. Computer readable data 420 may include, for example, configuration settings for the scanner 412, such as presets that instruct the processor 414 how to acquire Doppler signals in the area corresponding to the AI-predicted gate position, gate width, correction angle and/or color box.

The scanner 412 may include a communications module 422 connected to the processor 414. In the illustrated example, the communications module 422 may wirelessly transmit signals to and receives signals from the display device 6 along wireless communication link 424. The protocol used for communications between the scanner 412 and the display device 6 may be WiFi™ or Bluetooth™, for example, or any other suitable two-way radio communications protocol. The scanner 412 may operate as a WiFi™ hotspot, for example. Communication link 424 may use any suitable wireless network connection. In some embodiments, the communication link between the scanner 412 and the display device 6 may be wired. For example, the scanner 412 may be attached to a cord that may be pluggable into a physical port of the display device 6.

The display device 6 may be, for example, a laptop computer, a tablet computer, a desktop computer, a smart phone, a smart watch, spectacles with a built-in display, a television, a bespoke display or any other display device that is capable of being communicably connected to the scanner 412. The display device 6 may host a screen 8 and may include a processor 434, which may be connected to a non-transitory computer readable memory 436 storing computer readable instructions 438, which, when executed by the processor 434, cause the display device 6 to provide one or more of the functions of the system 400. Such functions may be, for example, the receiving of ultrasound data that may or may not be pre-processed; scan conversion of ultrasound data that is received into a ultrasound images; processing of ultrasound data in image data frames; the display of an ultrasound image on the screen 8; the display of a user interface elements; the control of the scanner 412; executing the software module that runs parallel to the standard ultrasound imaging software for tracking operator inputs of user interface elements related to the gate and/or color box; the storage, application, deployment, reinforcing and/or training of an AI model with respect to the placement of a gate and/or color box; and/or adjusting of ultrasound settings to correspond to the placement of the gate and/or color box.

Also stored in the computer readable memory 436 may be computer readable data 440, which may be used by the processor 434 in conjunction with the computer readable instructions 438 to provide the functions of the system 400. Computer readable data 440 may include, for example, settings for the scanner 412, such as presets for acquiring Doppler frames based on the AI-predicted user interface elements of the gate and/or color box; ultrasound data received from the scanner 412; settings for a user interface displayed on the screen 8; and/or one or more AI models. Settings may also include any other data that is specific to the way that the scanner 412 operates or that the display device 6 operates.

It can therefore be understood that the computer readable instructions and data used for controlling the system 400 may be located either in the computer readable memory 416 of the scanner 412, the computer readable memory 436 of the display device 6, and/or both the computer readable memories 416, 436.

The display device 6 may also include a communications module 442 connected to the processor 434 for facilitating communication with the scanner 412. In the illustrated example, the communications module 442 wirelessly transmits signals to and receives signals from the scanner 412 on wireless communication link 424. However, as noted, in some embodiments, the connection between scanner 412 and display device 6 may be wired.

Figure 5:
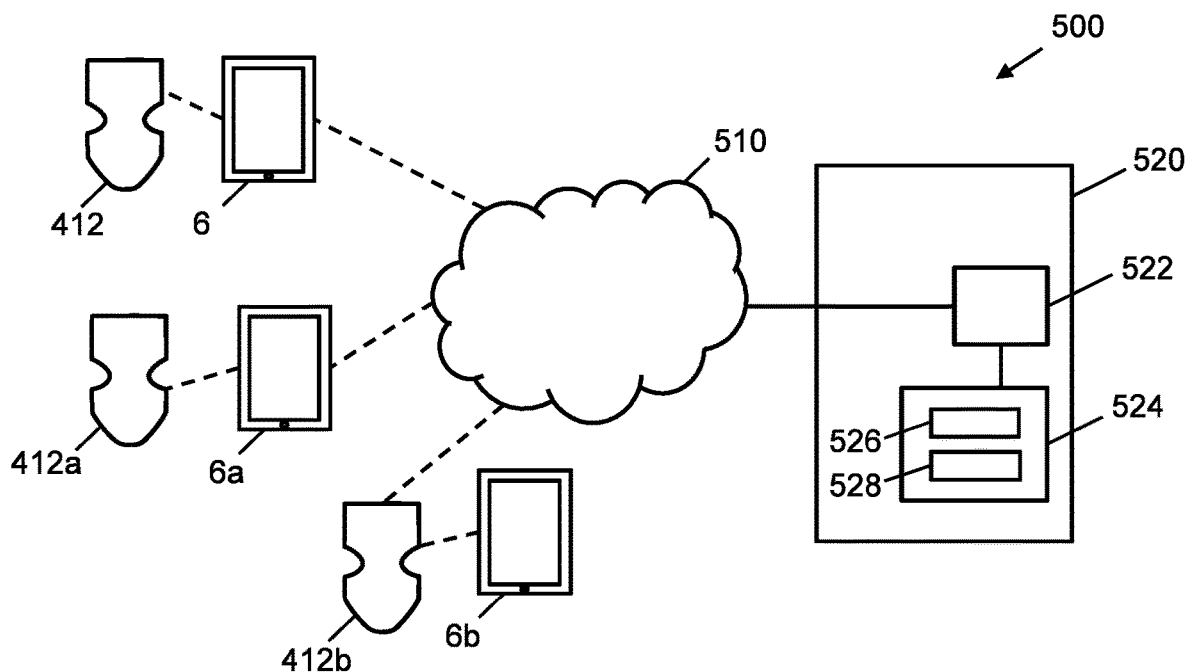
FIG. 5 is a schematic diagram of a distributed network of ultrasound imaging systems according to an embodiment of the present invention.

Referring to FIG. 5, a distributed network 500 is shown in which there are multiple similar or different scanners 412, 412a, 412b connected to their corresponding display devices 6, 6a, 6b and either connected directly, or indirectly via the display devices, to a communications network 510, such as the internet. The scanners 412, 412a, 412b may be connected onwards via the communications network 510 to a server 520.

The server 520 may include a processor 522, which may be connected to a non-transitory computer readable memory 524 storing computer readable instructions 526, which, when executed by the processor 522, cause the server 520 to provide one or more of the functions of the distributed network 500. Such functions may be, for example, the receiving of ultrasound data that may or may not be pre-processed, the scan conversion of ultrasound data that is received into an ultrasound image, the processing of ultrasound data in image data frames, the control of the scanners 412, 412a, 412b, and/or machine learning activities related to one or more AI models 206, 306 (as shown in FIGS. 2 and 3). Such machine learning activities may include the training and/or reinforcing of one or more AI models 206, 306.

Also stored in the computer readable memory 524 may be computer readable data 528, which may be used by the processor 522 in conjunction with the computer readable instructions 526 to provide the functions of the distributed network 500. Computer readable data 528 may include, for example, settings for the scanners 412, 412a, 412b such as preset parameters for acquiring ultrasound data, settings for user interfaces displayed on the display devices 6, 6a, 6b, and one or more AI models 206, 306. For example, one AI model may be an AI model for predicting locations for placement, width, and correction angle of gates and/or color boxes for Doppler signals used by the scanners 412, 412a, 412b. Settings may also include any other data that is specific to the way that the scanners 412, 412a, 412b operate or that the display devices 6, 6a, 6b operate.

It can therefore be understood that the computer readable instructions and data used for controlling the distributed network 500 may be located either in the computer readable memory of the scanners 412, 412a, 412b, the computer readable memory of the display devices 6, 6a, 6b, the computer readable memory 524 of the server 520, or any combination of the foregoing locations.

As the scanners 412, 412a, 412b and corresponding display devices 6, 6a, 6b may be different, the placement, sizing, and correction angle of the gates and/or the positioning of the color box (e.g., when using Doppler related modes) would generally be performed by different operators. This may allow the various inputs for training the AI models 206, 306 (as shown in FIGS. 2 and 3) to be more robust, since it is based on different user input. These various datasets can then be consolidated for training and/or reinforcing the AI models 206, 306 at the server 520. As the AI models 206, 306 are updated from time to time based on new training data collected at the various scanners 412, 412a, 412b and corresponding display devices 6, 6a, 6b, in some embodiments, AI models 206, 306 used at the display devices 6, 6a, 6b may be updated from the AI models 206, 306 present in the server 520.

Figure 7:
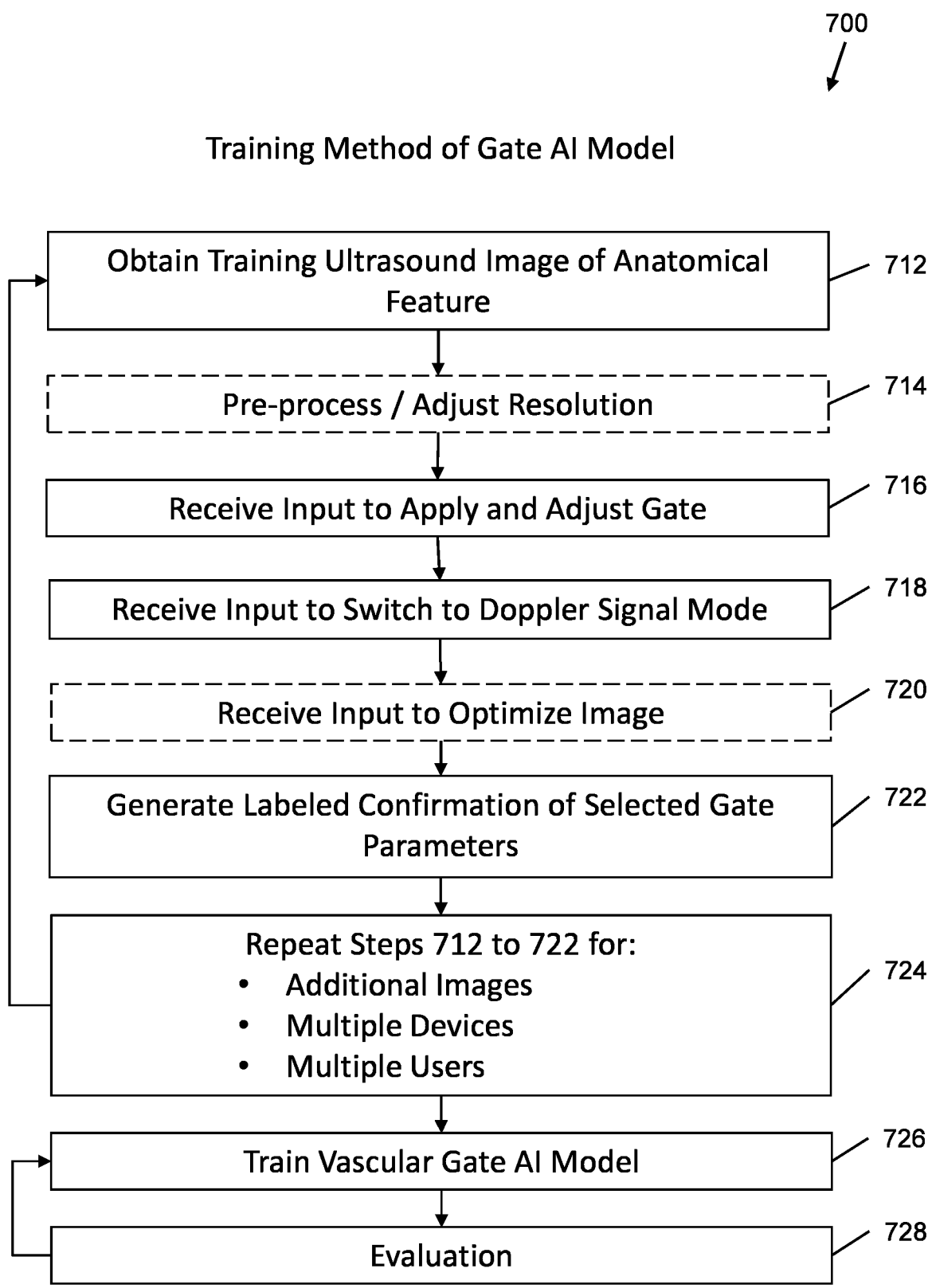
FIG. 7 is flowchart diagram of the steps for training a gate placement AI model, according to an embodiment of the present invention.

FIG. 7 is flowchart diagram of the steps for training the AI model of FIGS. 2 and 6, according to an embodiment of the present invention. Method 700 is described below with regard to the systems and components depicted in FIGS. 4 and 5, though it should be appreciated that method 700 may be implemented with other systems and components without departing from the scope of the present disclosure. In some embodiments, method 700 may be implemented as executable instructions in any appropriate combination of the imaging system 400, for example, an external computing device connected to the imaging system 400, in communication with the imaging system 400, and so on. As one example, method 700 may be implemented in non-transitory memory of a computing device, such as the controller (e.g., processor) of the imaging system 400 in FIG. 4. At 712, method 700 may include acquiring a dataset of sample images for training the neural network. Each sample image in the dataset may be a sample ultrasound image depicting an anatomical feature, for example a vascular feature (and more specifically here, for example, an artery).

Referring still to FIG. 7, in step 712, a training ultrasound image may be obtained. For example, a training ultrasound image may be acquired by the scanner 412 (as shown in FIG. 5) transmitting and receiving ultrasound energy. The training ultrasound image may be a post-scan converted ultrasound image. However, as discussed herein, it is to be made clear that the AI models of the present invention may be trained by B-mode ultrasound images and/or Doppler ultrasound images, without limitation. Furthermore, while the method of FIG. 7 is described in relation to a single training ultrasound image, the method may also apply to the use of multiple training ultrasound images. While the method of FIG. 7 is described in relation to a post-scan ultrasound image, it is to be understood that pre-scan images, may be used, as described in U.S. patent application Ser. No. 17/187,851 filed Feb. 28, 2021, the entire contents of which are incorporated herein by reference.

Optionally, in step 714 (as shown in dotted outline), the resolution of the training ultrasound image may be adjusted. For example, the resolution may be increased or decreased. The purpose of this may be to provide the labeler (e.g., a medical professional with relevant clinical expertise) with training ultrasound images that have a more standardized appearance. This may help to maintain a higher consistency with which the labeler identifies vascular features in the training ultrasound images. Besides the resolution, other parameters of the training ultrasound image may also be adjusted such as input scaling, screen size, pixel size, aspect ratio, and the removal of dead space, as described above (including, for example, data augmentation and other pre-processing steps).

In step 716, the training ultrasound image may be displayed on a display device, such as the display device 6 discussed above in relation to FIG. 5 and input is received to apply and adjust gate on the vascular feature. As the gate defines the size and location of the area from which Doppler information is obtained and it is delineated as a pair of crosshairs within the 2D image, an optimally trained gate, for any, for example, vascular feature, should be as small as possible to exclude erroneous signal arising from adjacent vessels or marginal flow. Too large a gate may admit erroneous signals from adjacent vessels and too small a gate may give the false impression of reduced or even absent flow. However, a smaller gate also reduces computation time and increases the frame rate, thereby allowing more accurate depiction of flow. To maximize depiction of flow, the gate should be positioned over the central part of the vascular feature in the ultrasound image. At step 716, such adjustments may be made as part of employing a plurality of ultrasound images to train the AI model.

At step 718, input is received to switch to Doppler signal mode. Optionally, at step 720 thereafter, each image may be optimized using, for example, flow detection, adjustments to color gain, adjustments to wall filters etc.

At step 722, the labeler can then identify a confirmation of optimal gate parameters. The labeler then can mark the training ultrasound image around the optimal gate (location, size and angle) that the labeler has identified in the training ultrasound image. In step 722, the system that is used for the training may receive the identification of optimized gate parameters and such system may generate, from the labeler's marking inputs, a labeled training ultrasound image, and display it on the display device.

Once the training ultrasound image has been marked and labeled, the system may then remove, optionally, regions of the labeled ultrasound data frame that are both outside the area of optimized gate and outside areas relevant for the AI model to recognize a placement location for the gate. For example, the labeled ultrasound data frame may be truncated at one or more sides. Truncation of some of the ultrasound data may allow the training of the AI model to proceed more quickly. At step 724, there is provided a redirection to complete steps 712-722 a plurality of times, for i) additional images from the same ultrasound device; ii) additional data from other ultrasound devices; and/or iii) additional images as acquired from multiple users, thereby to build a robust gate placement specific AI model. At step 726, the labeled raw ultrasound data frame is then used for training the AI model 206. At step 728, once training is completed, the AI model may be used to perform predictions on an unseen dataset to validate its performance, such evaluation at step 728 feeding data back to train the AI model at step 726.

As described herein, the AI models of the present invention may further be trained with image data conveyed from a cloud-based storage (e.g., previous exams stored on the cloud-based storage that may have indicated optimal gate placement. Further, the AI models of the present invention may further be trained as described in FIG. 11.

Figure 8:
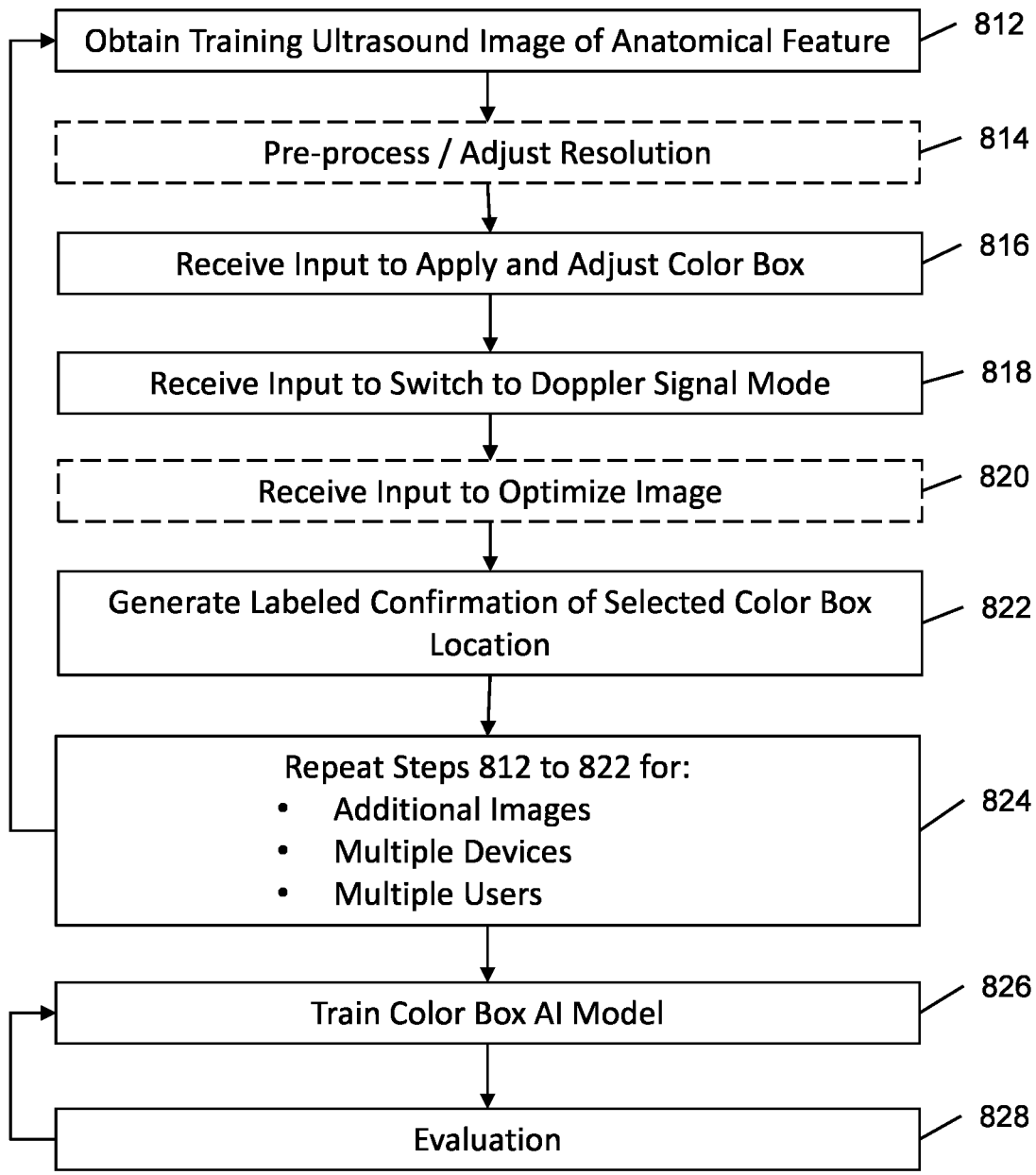
FIG. 8 is flowchart diagram of the steps for training a color box placement AI model, according to an embodiment of the present invention.

FIG. 8 is flowchart diagram of the steps for training the AI model of FIGS. 3 and 6, according to an embodiment of the present invention. Method 800 is described below with regard to the systems and components depicted in FIGS. 4 and 5, though it should be appreciated that method 800 may be implemented with other systems and components without departing from the scope of the present disclosure. In some embodiments, method 800 may be implemented as executable instructions in any appropriate combination of the imaging system 400, for example, an external computing device connected to the imaging system 400, in communication with the imaging system 400, and so on. As one example, method 800 may be implemented in non-transitory memory of a computing device, such as the controller (e.g., processor) of the imaging system 400 in FIG. 4. At 812, method 800 may include acquiring a dataset of sample images for training the neural network. Each sample image in the dataset may be a sample ultrasound image depicting for example, a vascular feature, more specifically, for example an artery.

Referring still to FIG. 8, in step 812, a training ultrasound image may be obtained. For example, a training ultrasound image may be acquired by the scanner 412 (as shown in FIG. 5) transmitting and receiving ultrasound energy. The training ultrasound image may be a post-scan converted ultrasound image. However, as discussed herein, it is to be made clear that the AI models of the present invention may be trained by B-mode ultrasound images and/or Doppler ultrasound images, without limitation. Furthermore, while the method of FIG. 8 is described in relation to a single training ultrasound image, the method may also apply to the use of multiple training ultrasound images. While the method of FIG. 8 is described in relation to a post-scan ultrasound image, it is to be understood that pre-scan images, may be used, as described in U.S. patent application Ser. No. 17/187,851 filed Feb. 28, 2021, the entire contents of which are incorporated herein by reference.

Optionally, in step 814 (as shown in dotted outline), the resolution of the training ultrasound image may be adjusted. For example, the resolution may be increased or decreased. The purpose of this may be to provide the labeler (e.g., a medical professional with relevant clinical expertise) with training ultrasound images that have a more standardized appearance. This may help to maintain a higher consistency with which the labeler identifies vascular features in the training ultrasound images. Besides the resolution, other parameters of the training ultrasound image may also be adjusted such as input scaling, screen size, pixel size, aspect ratio, and the removal of dead space, as described above (including, for example, data augmentation and other pre-processing steps).

In step 816, the training ultrasound image may be displayed on a display device, such as the display device 6 discussed above in relation to FIG. 5 and input is received to apply and adjust a color box on the vascular feature. The size, shape, and location of the color box are adjustable and define the volume of tissue from which color data are acquired. All velocity information from this defined volume of tissue is presented as color-encoded Doppler shifts in the image field. The frame rate decreases as box size increases, so image resolution and quality are affected by box size and width. Increasing the size or width will reduce the frame rate and increase the required processing power and time. Thus, in training an AI model for color box placement, adjustments at step 816 may be made accordingly. The color box overlay should be as small and superficial as possible while still providing the necessary information, thereby maximizing the sampling or frame rate. Too big an overlay reduces the frame rate and thus results in inferior depiction of flow. At step 816, all such adjustments may be made as part of employing a plurality of ultrasound images to train the AI model.

At step 818, input is received to switch to Doppler signal mode. Optionally, at step 820 thereafter, each image may be optimized using, for example, flow detection, adjustments to color gain, adjustments to wall filters etc.

At step 822, the labeler can then identify a confirmation of optimal color box location and size parameters. The labeler then can mark the training ultrasound image around the optimal color box location and size that the labeler has identified in the training ultrasound image. In step 822, the system that is used for the training may receive the identification of optimized color box location and size and such system may generate, from the labeler's marking inputs, a labeled training ultrasound image, and display it on the display device.

Once the training ultrasound image has been marked and labeled, the system may then remove, optionally, regions of the labeled ultrasound data frame that are both outside the area of optimized color box and outside areas relevant for the AI model to recognize a placement location for the color box. For example, the labeled ultrasound data frame may be truncated at one or more sides. Truncation of some of the ultrasound data may allow the training of the AI model to proceed more quickly. At step 824, there is provided a redirection to complete steps 812-822 a plurality of times, for i) additional images from the same ultrasound device; ii) additional data from other ultrasound devices; and/or iii) additional images as acquired from multiple users, thereby to build a robust color box placement specific AI model. At step 826, the labeled raw ultrasound data frame is then used for training the AI model 306. At step 828, once training is completed, the AI model may be used to perform predictions on an unseen dataset to validate its performance, such evaluation at step 828 feeding data back to train the AI model at step 826.

Figure 9:
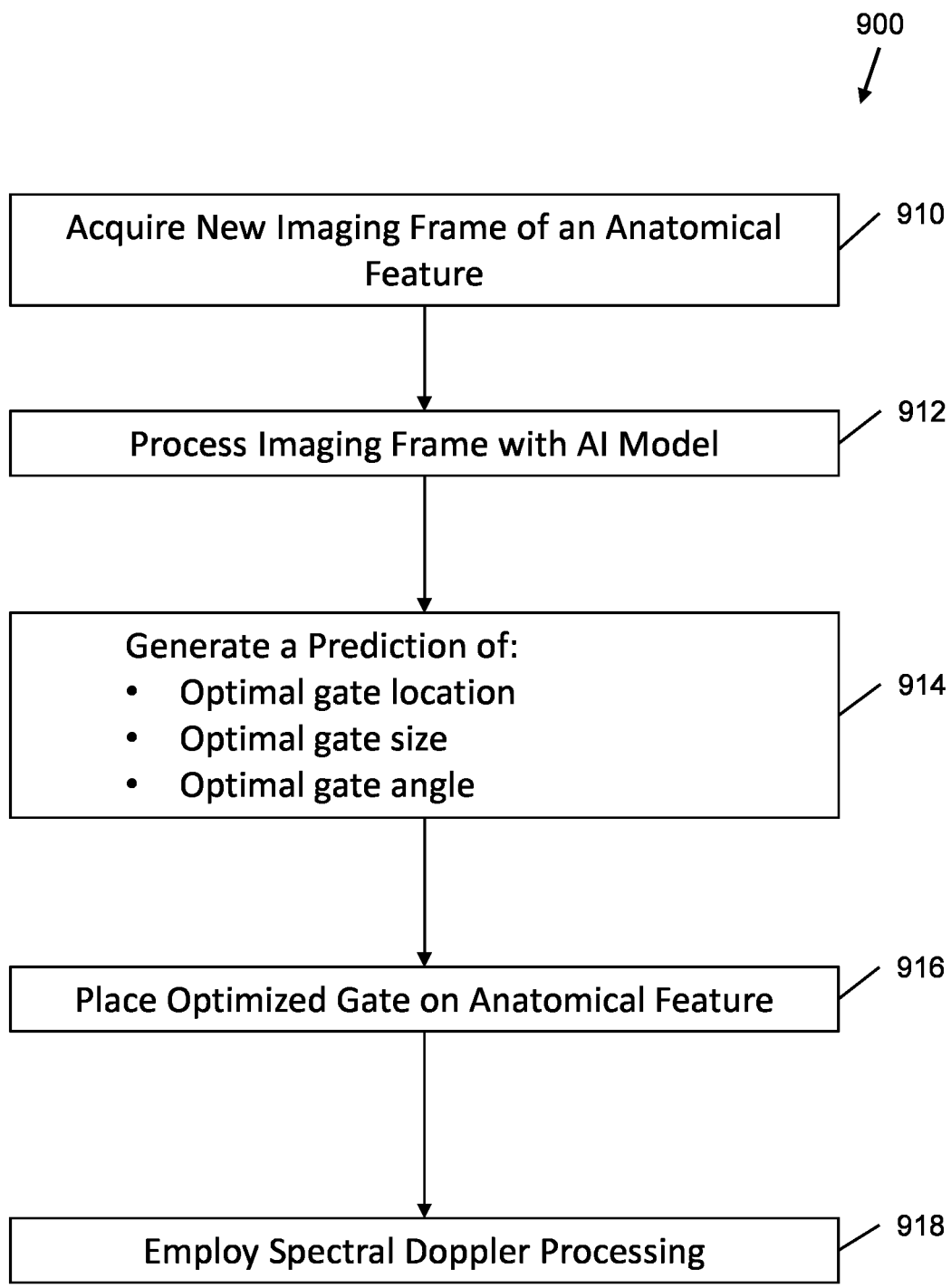
FIG. 9 is a flowchart diagram of an example method of image acquisition, processing employing an AI model, and placement of optimized gate (optimized gate parameters) on an anatomical feature shown in ultrasound image.

Referring to FIG. 9, a flowchart diagram of a method, generally indicated at 900, of new image acquisition of an anatomical feature, processing against an AI model and prediction of placement of optimal gate parameters, according to at least one embodiment of the present invention is shown. Method 900 further supports and aligns with elements 204, 210, 208, 207 and 212 described above in FIG. 2. At 910, the ultrasound imaging system (referred to in FIG. 4), may acquire ultrasound imaging data. For example, a medical professional may operate an ultrasound scanner (hereinafter "scanner", "probe", or "transducer" for brevity) to capture images of a patient (whether human or animal). The ultrasound frames (B-mode) may be acquired by acquiring a series of a images (with a frame each containing a sequence of transmitted and received ultrasound signals) of different views of a vascular feature.

Further, at step 910, new ultrasound imaging data may optionally be pre-processed and/or augmented as described above. At step 914, AI model 206 (FIG. 2) or collective AI model 622 (FIG. 6) generates a prediction of one or more of: i) optimal gate location; ii) optimal gate size; and iii) optimal gate angle to be applied to the feature imaged in the new ultrasound imaging data. Thereafter, at step 916, such predicted optimized gate is placed on the feature imaged in the new ultrasound imaging data and, at step 918, Spectral Doppler processing is employed.

Figure 10:
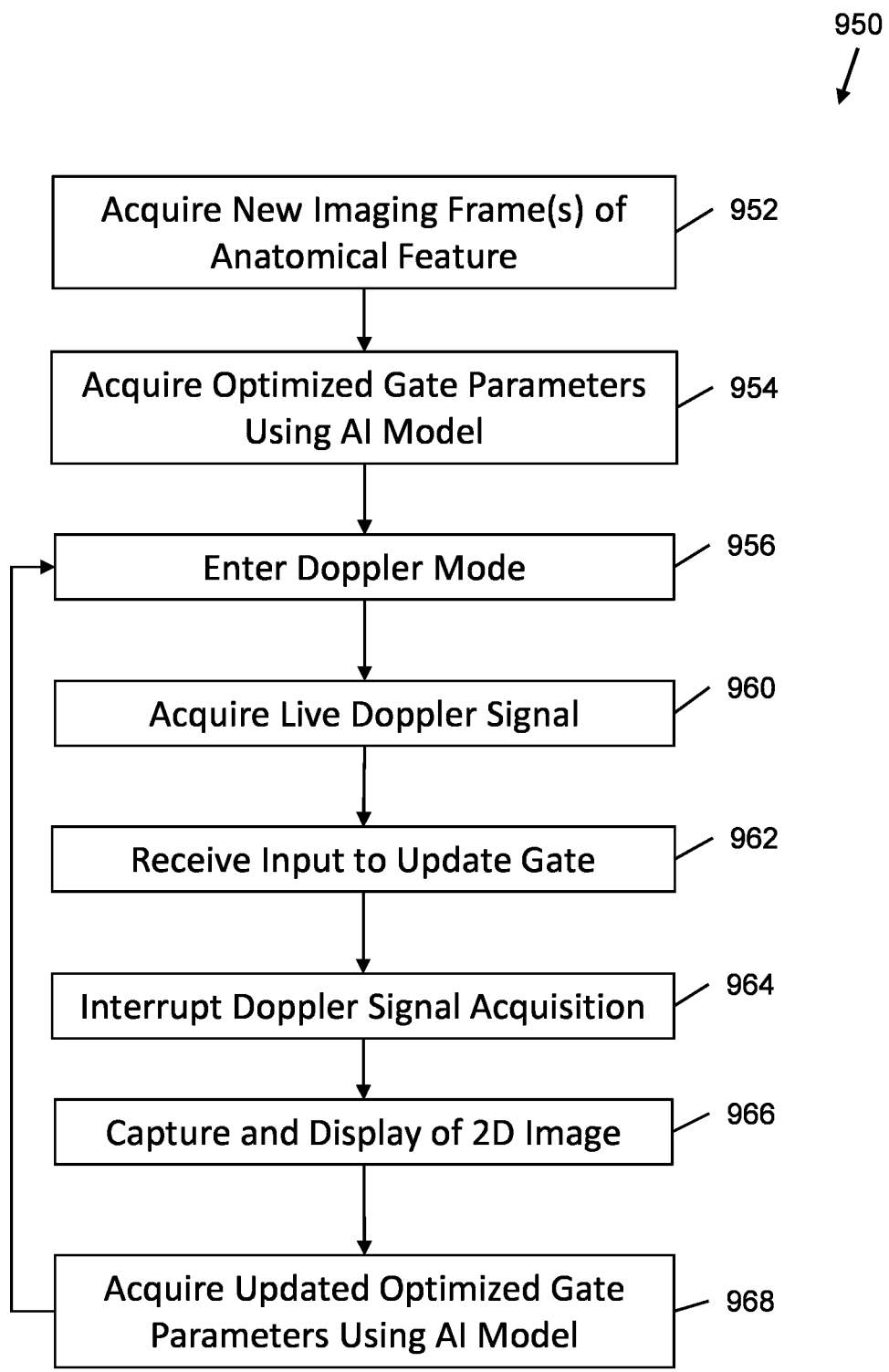
FIG. 10 is a flowchart diagram of an example method of image acquisition, processing employing an AI model, placement of optimized gate on an anatomical feature shown in ultrasound image, acquiring Doppler signal and subsequent interruption of Doppler signal to acquire updated optimized gate parameters, using AI model.

FIG. 10 is flowchart diagram of the method steps (shown generally as 950) for updating optimal gate parameters after interruption of Doppler signal acquisition, according to at least one embodiment of the present invention. At 952, the ultrasound imaging system (referred to in FIG. 4), may acquire ultrasound imaging data. These ultrasound frames may be acquired by acquiring a series of a images (with a frame each containing a sequence of transmitted and received ultrasound signals) of different views of, for example, a vascular feature. Further, at step 952, the ultrasound imaging data may optionally be pre-processed and/or augmented as described above. At step 954, AI model 206 (FIG. 2) or collective AI model 622 (FIG. 6) may generate a prediction of one or more of: i) optimal gate location; ii) optimal gate size; and iii) optimal gate angle to be applied to the anatomical feature imaged in the B-mode ultrasound imaging data. Thereafter, a predicted optimized gate is placed on the anatomical feature imaged in the ultrasound imaging data and, the system may receive an input at step 956 that causes it to enter spectral Doppler mode. In some instances, the acquisition of B-mode image frames stops, and the B-mode image feed is frozen, with the resultant B-mode image on a user interface being reduced in size to accommodate the spectral Doppler mode display portion (for example, 23 in FIGS. 12-14). In some instances, it is not possible to operate in duplex mode due to the particular anatomical feature being imaged, or due to physics or due to the pulse repetition frequency (PRF). In these and other instances, only the spectral Doppler mode display portion may be viewable on the user interface.

Regardless, it may be desirable to be able to update gate placement using the AI models of the present invention. In one aspect, the gate placement may be updated by user intervention, providing a direction to the processor to enable and engage updating steps, as described herein. In yet another embodiment, the gate may be updated (without user intervention) in response to a deficiency in the Spectral signal, the processor detecting such deficiency and automatically directing a gate placement reset, using the AI models of the present invention. Such deficiency may indicate that a readjustment of the gate is required for optimal signal processing in the spectral signal.

Referring still to FIG. 10, once spectral Doppler mode is entered at step 956, a live Doppler signal is acquired at step 960 and displayed on a user interface for viewing allowing the detected Doppler shifts (kHz) to be translated into velocities (m/s). The flow is displayed as a spectral waveform of changes in velocity wherein the flow velocity is the vertical axis with the time on the horizontal axis (see FIGS. 12-14). At step 962, there is a received an input to update the gate, which triggers a temporary interruption of the Doppler signal acquisition at step 964 and at step 966, a display on the user interface, of a captured a two-dimensional (2D) ultrasound image ("captured image"). At step 968, the AI model is applied to the captured image generate a prediction of one or more of an optimal updated gate position, size and angle (the "updated optimized gate") and the updated optimized gate is employed to enable corresponding SD-mode signals, therein to re-enter Doppler mode at back at step 956.

Figure 12:
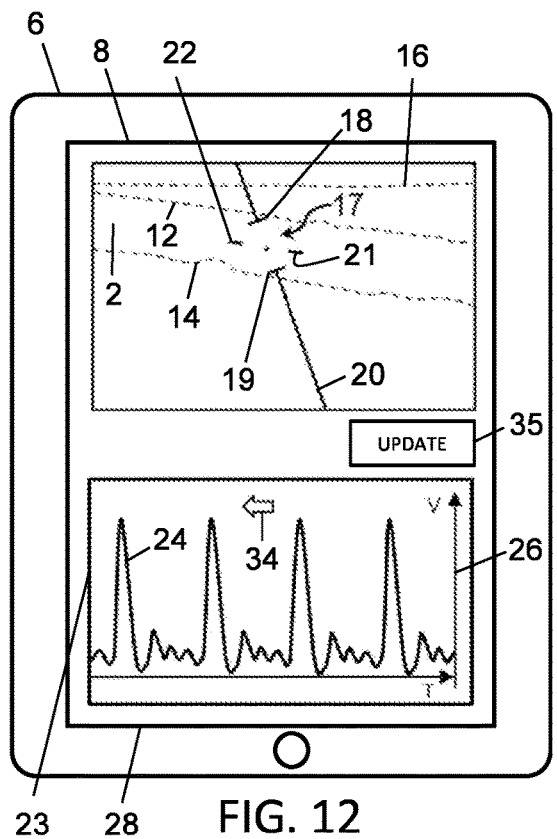
FIGS. 12-14 show a sequence of displays on the user interface as the system is switched between the PW Doppler mode and B-mode, for AI model updating of a gate on the anatomical feature, according to an embodiment of the present invention.
Figure 13:
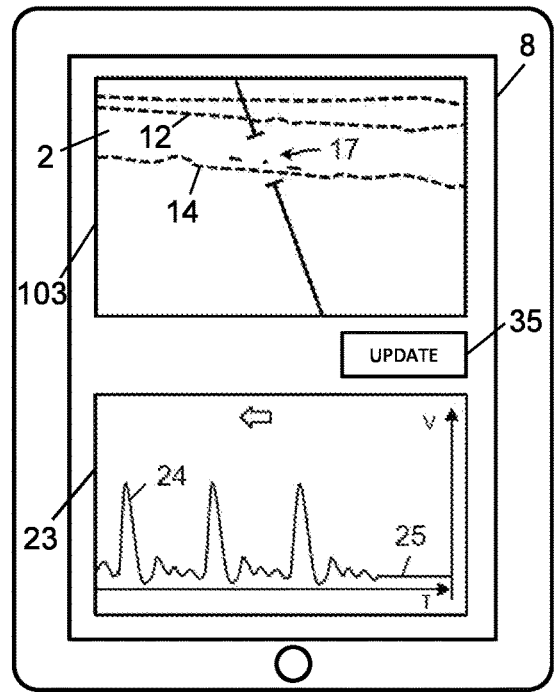
Figure 14:
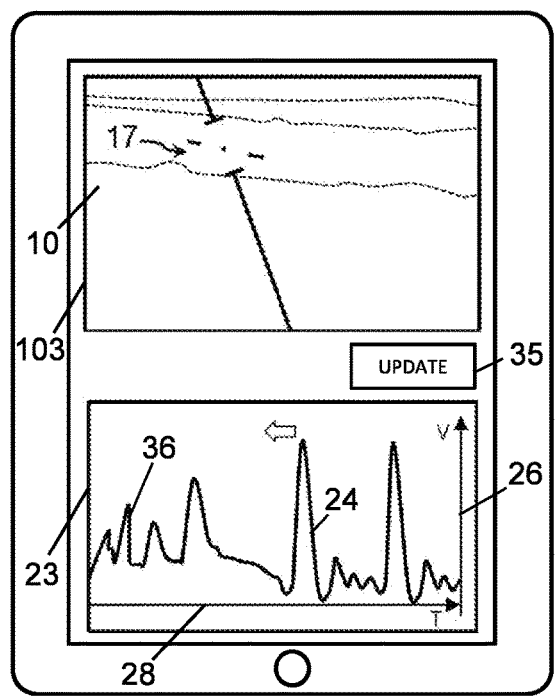

Referring to FIGS. 12-14, an exemplary sequence of displays on the touchscreen 8 is shown as the method of FIG. 10 is performed. Prior to the screenshot of FIG. 12, the system may be operating in a conventional B-mode operation (act 952 of FIG. 10). The system may then receive input to switch to a spectral Doppler mode (e.g., through navigation of a menu or some other user interface mechanism). In FIG. 12, the system 400 is in the spectral Doppler mode (act 960 of FIG. 10). The gate 17 is shown superimposed on the frozen B-mode image (act 954 of FIG. 10). The spectrum 24, in the Doppler mode display portion 23, is shown in a bold line as it is live and the live Doppler signal is being acquired (act 960 of FIG. 10).

In FIG. 13, the system 400 has received an input to temporarily interrupt the live Doppler signal for the purpose of an AI model-directed gate update (acts 962 and 964 of FIG. 10). Such input may be via Update Gate button 35 although as described herein, other input options are fully contemplated within the scope of the invention, including auto-updates by the processor in response of Spectral signal deficiency or interruption. A user/operator may have initiated this action for various reasons, for example, because the body being scanned has moved, the ultrasound scanner 412 has moved, and/or the spectrum 24 has changed in its displayed characteristics (e.g., diminished in amplitude). The mono, Doppler signal acquisition may then be interrupted (act 964 of FIG. 10) to allow for capture and display of a B-mode image (at act 966 of FIG. 10). Correspondingly, live synchronous B-mode images 10 may be displayed (this is shown as the B-mode image 10 having bold dashed lines in FIG. 13). The gate 17 is shown superimposed on the B-mode image 10 in the same relative position in the display area 103 as it was in FIG. 12 (pre-gate update). However, in the example screenshot of FIG. 13, it can be seen that the vessel on which the gate 17 was centered in FIG. 12 has now shifted in the live ultrasound image 10 so that the gate 17 is no longer in the optimal centered position. As a result, the gate 17 is no longer set in the originally desired location and orientation, and the Doppler mode signal that was being acquired immediately prior to switching to the B-mode was therefore likely to be less accurate than it could have been.

Referring still to FIG. 13, it can also be seen that the spectrum 24 in the Doppler mode display portion 23 is no longer acquiring a strong live signal (as shown in a light line in FIG. 13 in contrast to the bold line showing the live spectrum in FIG. 12). A weaker portion 25 of the spectrum 24 in FIG. 13 also shows that the acquisition of the Doppler signal has been fully or partially interrupted.

Act 968 of FIG. 10 provides for the acquisition of an AI model directed updated gate (one or more of: location, size and angle). System 400 continues to acquire B-mode frames and the B-mode image 10 remains live. Also, the position of the gate 17 (as shown in solid lines) has been adjusted (without any further user intervention) by AI model 206: from its original position relative to the display area 103 to an updated position (FIG. 14). Within the scope of the invention and this AI model directed gate updating, there is very little to no interruption to the spectral Doppler mode, as can be seen at 25 in FIGS. 13 and 36 in FIG. 14 (i.e. virtually no flatlining and quickly recovered amplitude). This benefit is achieved by the combination of the trained AI model for optimal gate placement and the expeditious B-mode image in response to a gate update request/input.

In FIG. 14, the gate has been updated using the AI model, the system 400 returns to the Doppler mode (act 956 of FIG. 10), and the B-mode image feed (on the user interface) is once again frozen. In the example screenshot of FIG. 14, this is shown with the B-mode image having lighter, dotted lines similar to FIG. 12. The updated gate 17 is superimposed on the B-mode image 10. In the Doppler mode display portion 23, the Doppler spectrum 24 reverts to a full live signal (act 960 of FIG. 10).

Figure 15:
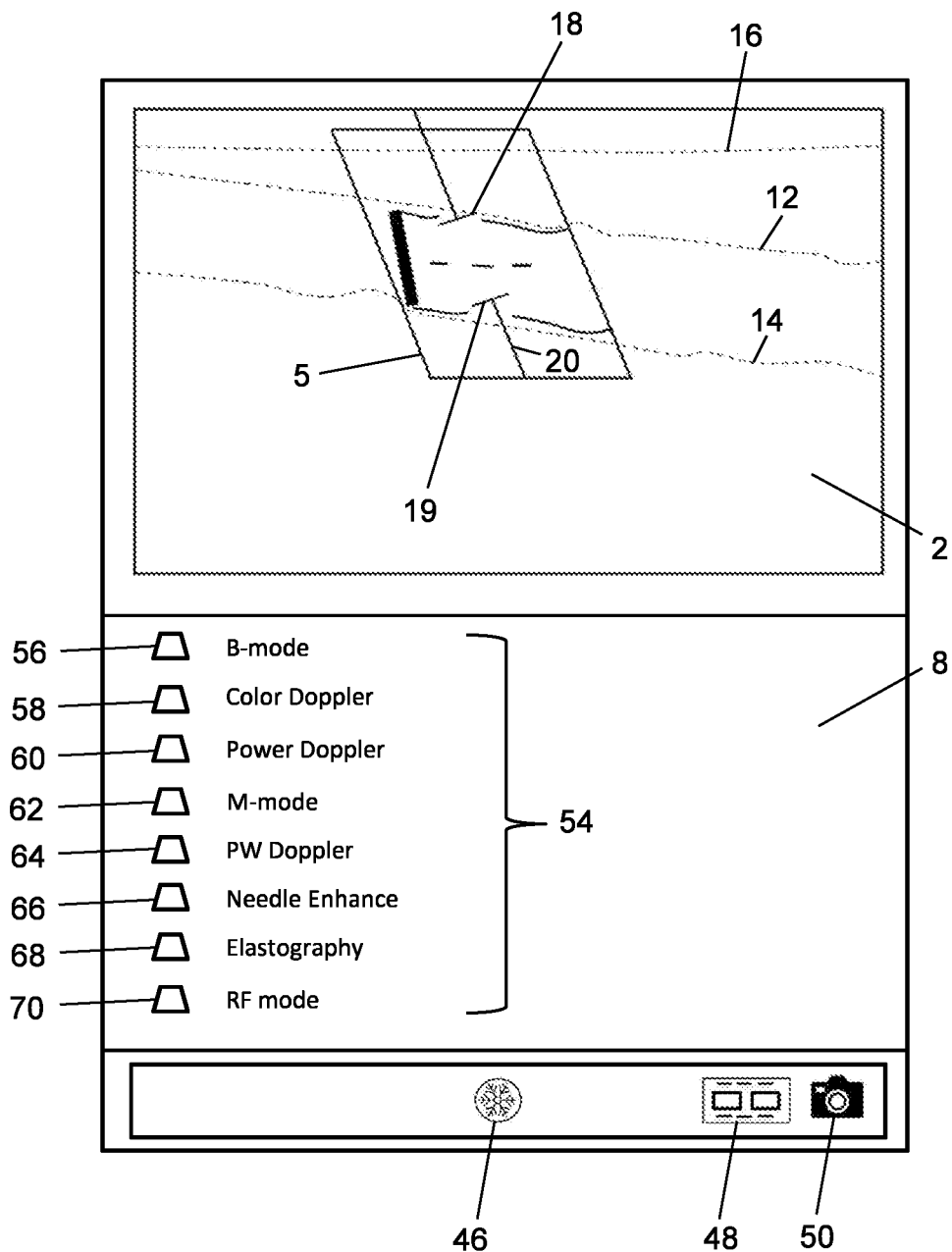
FIG. 15 is a touchscreen user interface showing a B-mode image, with AI model directed gate and color box placement, along with drop-down screen mode options, according to an embodiment of the present invention.

FIG. 15 is an exemplary display on touchscreen 8, showing frozen B-mode image 2, blood vessel walls 12 and 14, skin 16 over which AI model of the invention has placed color box 5 and gate 17 (comprising ends 18 and 19, and direction line 20). On screen 8 are exemplary user experience/interaction features such as freeze screen contact point 46, film contact point 48, photo capture contact point 50, along with a drop-down menu comprising a plurality of options including: B-mode 56, Color Doppler 58, Power Doppler 60, M-Mode 62, PW Doppler 64, Needle Enhance 66, Elastography 68, and RF Mode 70.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

B. Glossary of Terms

Unless the context clearly requires otherwise, throughout the description and the
   "comprise", "comprising", and the like are to be construed in an inclusive sense, as opposed to an exclusive or exhaustive sense; that is to say, in the sense of "including, but not limited to";
   "connected", "coupled", or any variant thereof, means any connection or coupling, either direct or indirect, between two or more elements; the coupling or connection between the elements can be physical, logical, or a combination thereof;
   "herein", "above", "below", and words of similar import, when used to describe this specification, shall refer to this specification as a whole, and not to any particular portions of this specification;
   "or", in reference to a list of two or more items, covers all of the following interpretations of the word: any of the items in the list, all of the items in the list, and any combination of the items in the list;
   the use of the masculine can refer to masculine, feminine or both;
   where numerical values are given, they are specified to the nearest significant figure;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

The term "2D-mode" refers to any ultrasound imaging mode that provides a two-dimensional cross-sectional view of body tissue, and may include B-mode, a combined B-mode/Color Doppler mode, or a combined B-mode/Power Doppler mode.

The term "B-mode" refers to the brightness mode of an ultrasound scanner, which displays the acoustic impedance of a two-dimensional cross-section of body tissue.

The term "Spectral Doppler" refers to a Doppler imaging mode of an ultrasound scanner using a single focused line to sample data at a given region (for example, in a blood vessel to visualize blood velocity).

The term "PW" refers to a pulsed wave Doppler imaging mode, which uses time of flight calculations to obtain signals from a given region, showing direction and speed through a one-dimensional spectrum that is updated over time.

The term "CW" refers to a continuous wave Doppler mode, which continuously transmits and receives at a single region to obtain signals, and can be used for high speed blood flow measurements.

The term "Color" or "Color Doppler" refers to a color Doppler imaging mode that characterizes blood flow across a 2-dimensional image, showing direction and speed.

The term "Power" or "Power Doppler" refers to a power Doppler imaging mode that characterizes blood flow across a 2-dimensional image, showing intensity but not direction or speed.

The term "AI model" means a mathematical or statistical model that may be generated through artificial intelligence techniques such as machine learning and/or deep learning. For example, these techniques may involve inputting labeled or classified data into a neural network algorithm for training, so as to generate a model that can make predictions or decisions on new data without being explicitly programmed to do so. Different software tools (e.g., TensorFlow™, PyTorch™, Keras™) may be used to perform machine learning processes.

The term "module" can refer to any component in this invention and to any or all of the features of the invention without limitation. A module may be a software, firmware or hardware module, and may be located, for example, in the ultrasound scanner, a display device or a server.

The term "communications network" can include both a mobile network and data network without limiting the term's meaning, and includes the use of wireless (e.g. 2G, 3G, 4G, 5G, WiFi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "operator" (or "user") may refer to the person that is operating an ultrasound scanner (e.g., a clinician, medical personnel, a sonographer, ultrasound student, ultrasonographer and/or ultrasound technician).

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to an ultrasound imaging system, the system being a subject of the present invention. In various embodiments, the system may include an ultrasound machine (including a display and one or more transducers); an ultrasound scanner and a display device; and/or an ultrasound scanner, display device and a server.

The term "ultrasound image frame" (or "image frame" or "ultrasound frame") refers to a frame of post-scan conversion data that is suitable for rendering an ultrasound image on a screen or other display device.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

C. Claim Support

In a first broad aspect of the present disclosure, there is provided a method for positioning a gate on an ultrasound image generated during scanning of an anatomical feature using an ultrasound scanner, said gate at least defining an optimal location of a Doppler mode signal in a tissue, the method comprising: deploying an artificial intelligence (AI) model to execute on a computing device communicably connected to the ultrasound scanner, wherein the AI model is trained so that when the AI model is deployed, the computing device generates a prediction of at least one of an optimal position, size, or angle for the gate on the ultrasound image generated during ultrasound scanning of the anatomical feature; acquiring, at the computing device, a new ultrasound image during ultrasound scanning; processing, using the AI model, the new ultrasound image to generate a prediction of one or more of an optimal gate position, size and angle (the "predicted optimized gate"); and employing the predicted optimized gate to enable corresponding Doppler mode signals.

In some embodiments, the method additionally comprises reprocessing the AI model against subsequently acquired ultrasound images at pre-determined intervals to update the predicted optimized gate. In some embodiments, the update is acceptable only within a confidence threshold.

In some embodiments, the method additionally comprises reprocessing the AI model to against subsequently acquired ultrasound images to update the predicted optimized gate, such reprocessing being triggered when at least one of the gate position, size and angle has changed beyond a threshold amount with respect to the subsequently acquired ultrasound images.

In some embodiments, the method comprises training the AI model using ultrasound images generated in one of B-mode (two-dimensional imaging mode) and Doppler mode.

In some embodiments, the method additionally comprises, a method of updating the gate as follows: displaying on a user interface of the computing device a live spectral Doppler mode ("SD-mode") ultrasound spectrum that corresponds to the predicted optimized gate; receiving input to update to a new predicted optimized gate; capturing a two-dimensional (2D) imaging mode ("2D mode") ultrasound image ("captured image"); applying the AI model to the captured image to generate a prediction of one or more of an optimal updated gate position, size and angle (the "updated optimized gate"); employing the updated optimized gate to enable corresponding SD-mode signals; and displaying a live-SD mode ultrasound spectrum that corresponds to the updated optimized gate.

In some embodiments, the method additionally provides that receiving input may be via at least one of the following modalities: a button, a touch-sensitive region of the user interface, a dial, a slider, a drag gesture, a voice command, a keyboard, a mouse, a trackpad, a touchpad, or any combination thereof.

In some embodiments, the method comprises training the AI model with one or more of the following: i) supervised learning; ii) previously labelled ultrasound image datasets; and iii) cloud stored data.

In some embodiments, the method comprises training the AI model with a plurality of training ultrasound frames, each of said training ultrasound frames comprising a mask created in Doppler mode, from a plurality of manual inputs, which mask defines optimal gate parameters.

In some embodiments, the method provides that, when processing the new ultrasound image using the AI model, the ultrasound imaging data is processed on at least one of: i) a per pixel basis, and the probability of optimal gate placement is generated on a per pixel basis and ii) a line sample basis, and the probability of optimal gate placement is generated on a line sample basis.

In some embodiments, the method provides that the anatomical feature is selected from group consisting of carotid artery, subclavian artery, axillary artery, brachial artery, radial artery, ulnar artery, aorta, hypergastic artery, external iliac artery, femoral artery, popliteal artery, anterior tibial artery, arteria *dorsalis* celiac artery, cystic artery, common hepatic artery (hepatic artery proper, gastric duodenal artery, right gastric artery), right gastroepiploic artery, superior pancreaticoduodenal artery, inferior pancreaticoduodenal artery, pedis artery, posterior tibial artery, ophthalmic artery, retinal artery, heart (including fetal heart) and umbilical cord.

In a second broad aspect of the present disclosure, there is provided a method for positioning a color box on an ultrasound image generated during ultrasound scanning of an anatomical feature, said color box at least defining an optimal location of a color Doppler mode signal in a tissue, the method comprising: deploying an artificial intelligence (AI) model to execute on a computing device communicably connected to the ultrasound scanner, wherein the AI model is trained so that when the AI model is deployed, the computing device generates a prediction of optimal color box placement for the color box, on the ultrasound image, during ultrasound scanning of the anatomical feature; acquiring, at the computing device, a new ultrasound image during ultrasound scanning; processing, using the AI model, the new ultrasound image to generate a prediction of the optimal new color box position; and employing the new color box position to enable corresponding color Doppler mode signals.

In a third broad aspect of the present disclosure, there is provided a method for employing an AI model which is trained both: i) to identify at least one of an optimal position, size, and angle of trained gates in ultrasound imaging data, such that when deployed, the computing device generates a prediction of at least one of an optimal position, size, and angle for a new gate on a new ultrasound image, during ultrasound scanning of an anatomical vascular feature and ii) to identify, with regard to tissue, an optimal placement of the color box on ultrasound imaging data such that when deployed, the computing device generates a prediction of optimal color box placement for a new color box, on a new ultrasound image, during ultrasound scanning of the anatomical feature, such AI model (the "combined AI model") predicting both optimal gate characteristics and color box location to employ corresponding Doppler mode signals.

In a fourth broad aspect of the present disclosure, there is provided an ultrasound system for automatically positioning a gate on an ultrasound image, during ultrasound scanning of an anatomical feature using an ultrasound scanner, said gate at least defining an optimal location of a Doppler mode signal in a tissue, said ultrasound system comprising: an ultrasound scanner configured to acquire a plurality of new ultrasound frames; a processor that is communicatively connected to the ultrasound scanner and configured to: process each new ultrasound frame of a plurality of new ultrasound frames against an artificial intelligence ("AI") model, wherein said AI model is trained so that when the AI model is deployed, it identifies at least one of an optimal position, size, and angle of a trained gate in the ultrasound imaging data; acquire the new ultrasound image during ultrasound scanning; process, using the AI model, the new ultrasound image to generate a prediction of one or more of the optimal new gate position, size and angle (the "predicted optimized gate"); employ the predicted optimized gate to enable corresponding Doppler mode signals; and a display device configured to display one or more of the ultrasound frames and the Doppler mode signals to a system user.

In some embodiments, in the ultrasound system, the display device comprises a user interface comprising: i) an input module that is communicatively connected to the ultrasound scanner, while the ultrasound scanner is operating in SD-mode; ii) a live SD-mode ultrasound spectrum that corresponds to the predicted optimized gate; said input module providing direction to the processor to update to a new predicted optimized gate such that user interface additionally displays iii) a captured a two-dimensional (2D) ultrasound image ("captured image") to which is applied a prediction of an optimal updated gate position, size and angle (the "updated optimized gate"); and iv) a live-SD mode ultrasound spectrum that corresponds to the updated optimized gate.

In some embodiments, in the ultrasound system, the AI model is trained with a plurality of training ultrasound frames, each of said training ultrasound frames comprising a mask created in Doppler mode, from a plurality of manual inputs, which mask defines optimal gate parameters.

In a fifth broad aspect of the present disclosure, there is provided a computer-readable media storing computer-readable instructions, for automatically positioning a gate on an ultrasound image, during ultrasound scanning of an anatomical feature using an ultrasound scanner, said gate at least defining an optimal location of a Doppler mode signal in a tissue, said computer-readable media storing computer-readable instructions, when executed by a processor cause the processor to: process each ultrasound frame of a plurality of ultrasound frames against an artificial intelligence ("AI") model, wherein said AI model is trained so that when it is deployed, it identifies at least one of an optimal position, size, and angle of a trained gate in ultrasound imaging data; acquire a new ultrasound image during ultrasound scanning; process, using the AI model, the new ultrasound image to generate a prediction of one or more of the optimal new gate position, size and angle (the "predicted optimized gate"); and employ the predicted optimized gate to enable corresponding Doppler mode signals.

In some embodiments, in the computer-readable media storing computer-readable instructions, the AI model is trained with a plurality of training ultrasound frames, each of said training ultrasound frames comprising a mask created in Doppler mode, from a plurality of manual inputs, which mask defines optimal gate parameters.

In a sixth broad aspect of the present disclosure, there is provided a portable computing device for updating a gate on an ultrasound scanner comprising: a user interface comprising i) an input module that is communicatively connected to the ultrasound scanner, while the ultrasound scanner is operating in SD-mode; ii) a live SD-mode ultrasound spectrum that corresponds to a previously predicted optimized gate; said input module providing direction to a processor to update to a new predicted optimized gate such that the user interface additionally displays iii) a captured a two-dimensional (2D) ultrasound image ("captured image") to which is applied a prediction of an optimal updated gate position, size and angle (the "updated optimized gate"); and iv) a live-SD mode ultrasound spectrum that corresponds to the updated optimized gate.

In a seventh broad aspect of the present disclosure, there is provided a computer-readable media storing computer-readable instructions, for automatically positioning a color box on a new ultrasound image, during B-ultrasound scanning of an anatomical feature using an ultrasound scanner, said color box at least defining an optimal location of a Doppler mode signal in a tissue, said computer-readable media storing computer-readable instructions, when executed by a processor cause the processor to: process each ultrasound frame of a plurality of ultrasound frames against an artificial intelligence ("AI") model, wherein said AI model is trained so that when the AI model is deployed, it identifies an optimal color box placement in ultrasound imaging data; acquire a new ultrasound image during ultrasound scanning; process, using the AI model, the new ultrasound image to generate a prediction of an optimal color box placement for the color box; employ the new color box to enable corresponding Doppler mode signals.

What is claimed is:

1. A method comprising:
    deploying a neural network configured with an artificial intelligence (AI) model to execute on a computing device communicably connected to an ultrasound scanner, wherein the neural network configured with the AI model is trained to identify, in an ultrasound image comprising a blood vessel, a gate position and at least one of a gate size and a gate angle, by delineating the gate from other non-gate image areas;
    acquiring, at the computing device via the ultrasound scanner, a new ultrasound image of an imaged blood vessel;
    processing, using the neural network configured with the AI model, the new ultrasound image, wherein the neural network configured with the AI model identifies and generates a predicted gate having a gate position and at least one of a gate size and a gate angle, by delineating the gate from other non-gate image areas, wherein the at least one of the gate size and gate angle match the imaged blood vessel in the new ultrasound image;
    employing the predicted gate to enable corresponding Doppler mode signals; and
    displaying the Doppler mode signals; and
    displaying the new ultrasound image with the predicted gate, having the at least one of the gate size and the gate angle matching the imaged blood vessel, superimposed on the imaged blood vessel.

2. The method of claim 1 additionally comprising processing subsequently acquired ultrasound images at predetermined intervals against the neural network configured with the AI model to update the predicted gate.

3. The method of claim 1 comprising training the neural network configured with the AI model using ultrasound images generated in one of B-mode and Doppler mode.

4. The method of claim 1 additionally comprising a method of determining an updated new gate as follows:
    displaying on a user interface of the computing device a live spectral Doppler mode ultrasound spectrum that corresponds to the predicted gate;
    receiving input to update to a new gate;
    capturing a subsequent ultrasound image;
    applying the neural network configured with the AI model to the captured subsequent ultrasound image to generate a prediction of an updated gate having an updated position and at least one of an updated gate size and updated gate angle;
    employing the updated gate as predicted to enable corresponding spectral Doppler-mode signals; and
    displaying a live-spectral Doppler mode ultrasound spectrum that corresponds to the updated gate.

5. The method of claim 4 wherein the input is user directed and is via at least one of the following modalities: a button, a touch-sensitive region of the user interface, a dial, a slider, a drag gesture, a voice command, a keyboard, a mouse, a trackpad, a touchpad, or any combination thereof.

6. The method of claim 1 comprising training the neural network configured with the AI model with one or more of the following: i) supervised learning; ii) previously labelled ultrasound image datasets; and iii) cloud stored data.

7. The method of claim 1 comprising training the neural network configured with the AI model with a plurality of training ultrasound frames, each of said training ultrasound frames comprising a mask created in Doppler mode, from a plurality of manual inputs, which mask defines gate parameters.

8. The method of claim 1 wherein, when processing the new ultrasound image of the imaged blood vessel using the neural network configured with the AI model, the new ultrasound image is processed on at least one of: i) a per pixel basis, and the probability of gate placement is generated on a per pixel basis and ii) a line sample basis, and the probability of gate placement is generated on a line sample basis.

9. The method of claim 1 wherein the blood vessel is selected from group consisting of carotid artery, subclavian artery, axillary artery, brachial artery, radial artery, ulnar artery, aorta, hypergastic artery, external iliac artery, femoral artery, popliteal artery, anterior tibial artery, arteria dorsalis celiac artery, cystic artery, common hepatic artery, hepatic artery proper, gastric duodenal artery, right gastric artery, right gastroepiploic artery, superior pancreaticoduodenal artery, inferior pancreaticoduodenal artery, pedis artery, posterior tibial artery, ophthalmic artery, retinal artery, non-fetal heart, and umbilical cord.

10. The method of claim 2, wherein the update is acceptable only within a confidence threshold.

11. The method of claim 2 comprising processing the subsequently acquired ultrasound images against the neural network configured with the AI model to update the gate, such processing being triggered when a subsequent gate position and at least one of, a subsequent gate size and a subsequent gate angle in the subsequent ultrasound images has changed beyond a threshold amount as compared to the gate position and at least one of, the gate size and the gate angle in the ultrasound images with the predicted gate.

12. The method of claim 4 wherein the input is not user directed and is generated in response to a deficiency in the spectral Doppler mode ultrasound signals.

13. The method of claim 4 wherein the captured subsequent ultrasound image is frozen while the live-spectral Doppler mode ultrasound spectrum is displayed.

* * * * *